(12) United States Patent
Morgan

(10) Patent No.: US 10,494,412 B2
(45) Date of Patent: Dec. 3, 2019

(54) PEPTIDES

(71) Applicant: HOX THERAPEUTICS LIMITED, Ashtead, Surrey (GB)

(72) Inventor: Richard Morgan, Bradford (GB)

(73) Assignee: HOX THERAPEUTICS LIMITED, Ashtead, Surrey (GB)

( * ) Notice: Subject to any disclaimer, the term of this patent is extended or adjusted under 35 U.S.C. 154(b) by 0 days.

(21) Appl. No.: 15/770,023

(22) PCT Filed: Oct. 20, 2016

(86) PCT No.: PCT/GB2016/053282
§ 371 (c)(1),
(2) Date: Apr. 20, 2018

(87) PCT Pub. No.: WO2017/068353
PCT Pub. Date: Apr. 27, 2017

(65) Prior Publication Data
US 2018/0282384 A1    Oct. 4, 2018

(30) Foreign Application Priority Data

Oct. 21, 2015 (GB) .................................. 1518700.8

(51) Int. Cl.
| | | |
|---|---|---|
| A61K 38/00 | (2006.01) | |
| C07K 14/47 | (2006.01) | |
| A61K 38/17 | (2006.01) | |
| A61K 45/06 | (2006.01) | |

(52) U.S. Cl.
CPC ...... *C07K 14/4702* (2013.01); *A61K 38/1709* (2013.01); *A61K 45/06* (2013.01); *A61K 38/00* (2013.01); *C07K 2319/10* (2013.01)

(58) Field of Classification Search
None
See application file for complete search history.

(56) References Cited

U.S. PATENT DOCUMENTS

| | | | |
|---|---|---|---|
| 5,595,756 A * | 1/1997 | Bally ................... | A61K 9/1272 264/4.1 |
| 5,608,082 A | 3/1997 | Vamey et al. | |
| 6,235,764 B1 | 5/2001 | Larson et al. | |
| 6,534,524 B1 | 3/2003 | Kania et al. | |
| 6,573,293 B2 | 6/2003 | Tang et al. | |
| 6,682,736 B1 | 1/2004 | Hanson et al. | |
| 7,259,266 B2 | 8/2007 | Carter et al. | |
| 2005/0148627 A1 | 7/2005 | Carter et al. | |
| 2005/0148777 A1 | 7/2005 | Carter et al. | |

FOREIGN PATENT DOCUMENTS

| | | |
|---|---|---|
| EP | 0 239 362 A2 | 9/1987 |
| WO | WO 01/40217 A1 | 6/2001 |
| WO | WO 02/053596 A2 | 7/2002 |
| WO | WO 2004/020431 A2 | 3/2004 |
| WO | WO 2004/055049 A1 | 7/2004 |
| WO | WO 2007/000601 A2 | 1/2007 |

OTHER PUBLICATIONS

Sporn et at,"Chemoprevention of Cancer," Carcinogenesis, vol. 21 (2000), 525-530 (Year: 2000).*
Gura, "Cancer Models:Systems for Identifying New Drugs Are Often Faulty," Science vol. 278 (1997), 1041-1042 (Year: 1997).*
Derossi et al., "Trojan peptides: the penetratin system for intracellular delivery," *Trends in Cell Biology* 8(2): 84-87 (1998).
Fields et al., "Solid phase peptide synthesis utilizing 9-fluorenylmethoxycarbonyl amino acids," *Int J Peptide Protein Res* 35(3): 161-214 (1990).
Krumlauf, "*Hox* genes in vertebrate development," *Cell* 78(2): 191-201 (1994).
Lindgren et al., "Cell-penetrating peptides," *Trends in Pharmacological Science* 21(3): 99-103 (2000).
Mann et al., "Extra specificity from *extradenticle*: the partnership between HOX and PBX/EXD homeodomain proteins," *Trends Genet.* 12(7): 258-262 (1996).
Merrifield et al., "Solid-phase peptide synthesis," *Adv Enzymol* 32: 221-296 (1969).
Morgan et al., "Identifying HOX paralog groups by the PBX-binding region," *Trends Genet.* 16(2): 66-67 (2000).
Morgan et al., Targeting the HOX/PBX dimer in breast cancer, *Breast Cancer Res Treat* 136(2): 389-398 (2012).
U.S. Appl. No. 61/113547, filed Dec. 23, 1998, Hanson et al.
Bessalle et al., "Structure-function studies of amphiphilic antibacterial peptides," *Journal of Medicinal Chemistry* 36(9): 1203-1209 (1993).
Daniels et al., "Disruption of HOX activity leads to cell death that can be enhanced by the interference of iron uptake in malignant B cells," *Leukemia* 24: 1555-1565 (2010).

(Continued)

*Primary Examiner* — Jeanette M Lieb
(74) *Attorney, Agent, or Firm* — Leydig, Voit & Mayer, Ltd.

(57) ABSTRACT

The present invention relates to novel peptides, which impair PBX-dependent regulation of gene transcription and thus have utility in the treatment or prevention of disorders in which aberrant cell division occurs. In particular, the invention provides a peptide comprising the amino acid sequence (I): $Y^1X^1X^2KWX^3X^4X^5X^6X^7Y^2$ (I) wherein the sequence $X^1$ to $X^7$ is an amino acid sequence comprising at least 7 amino acids, which may optionally be interrupted by one or two amino acid residues between one or more of the 9 amino acid positions defined herein; $X^1$ is selected from W, T, PE, KQI, W, PQT, H, R1 and absent; $X^2$ is an amino acid with an aromatic side chain or cysteine; $X^3$ is a hydrophobic amino acid $X^4$ is an amino acid with a charged side chain; $X^5$ is an amino acid with a basic side chain; $X^6$ is an amino acid or absent; $X^7$ is one or more amino acids or absent; and $Y^1$ and $Y^2$ are each either absent or a peptide comprising a cationic polymer of basic amino acids, provided that at least one of $Y^1$ and $Y^2$ is present.

26 Claims, 11 Drawing Sheets

Specification includes a Sequence Listing.

(56) References Cited

OTHER PUBLICATIONS

Errico et al., "The abrogation of the HOXB7/PBX2 complex induces apoptosis in melanoma through the miR-221&222-c-FOS pathway," *Int J Cancer 133*(4): 879-892 (2013).
Morgan et al., "Antagonism of HOX/PBX Dimer Formation Blocks the In vivo Proliferation of Melanoma," *Cancer Research 67*(12): 5806-5813 (2007).
Morgan et al., "Targeting HOX and PBX transcription factors in ovarian cancer," *BMC Cancer 10*(89):1-9 (2010).
Morgan et al., "Targeting *HOX* transcription factors in prostate cancer," *BMC Urology 14*: 17 (9 pages) 2014.
Plowright et al., "HOX transcription factors are potential therapeutic targets in non-small-cell lung cancer (targeting HOX genes in lung cancer)," *Br. J. Cancer 100*(3): 470-475 (2009).
*Remington'S Pharmaceutical Sciences*, 18th Edition, Mack Printing Co. (1990) pp. 1289-1329.
Shanmugam et al., "Residues Flanking the HOX YPWM Motif Contribute to Cooperative Interactions with PBX," *Journal of Biological Chemistry 272*(30): 19081-19087 (1997).
Shears et al., "Disrupting the Interaction Between HOX and PBX Causes Necrotic and Apoptotic Cell Death in the Renal Cancer Lines CaKi-2 and 769-P," *J Urol 180*(5): 2196-2201 (2008).
Sprules et al., "Lock and Key Binding of the HOX YPWM Peptide to the PBX Homeodomain," *Journal of Biological Chemistry 278*(2): 1053-1058 (2003).
European Patent Office, International Search Report in International Application No. PCT/GB2016/053282 (dated Feb. 3, 2017).
European Patent Office, Written Opinion in International Application No. PCT/GB2016/053282 (dated Feb. 3, 2017).
International Bureau of WIPO, International Preliminary Report on Patentability in International Application No. PCT/GB2016/053282 (dated Apr. 24, 2018).

\* cited by examiner

Figures 1A-1D: Effect of peptides on cell viability *in vitro*

Figure 2: Cells stained with DAPI (a); incubated with HTL001-FITC (b); and the resulting composite image (c). HTL001/7FAM5 enters the cytoplasm and nuclei of PC3 cells in vitro after being incubated with 1.3 μM of FAM5 labelled HTL001 (green) for 2 hours. The cell nuclei were stained using DAPI (blue). Magnification x40
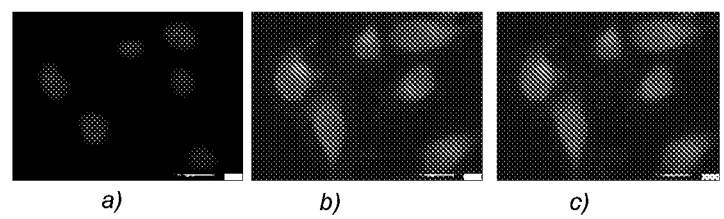
a)    b)    c)

Figure 3: cFOS expression in PC3 cells after HTL001 treatment
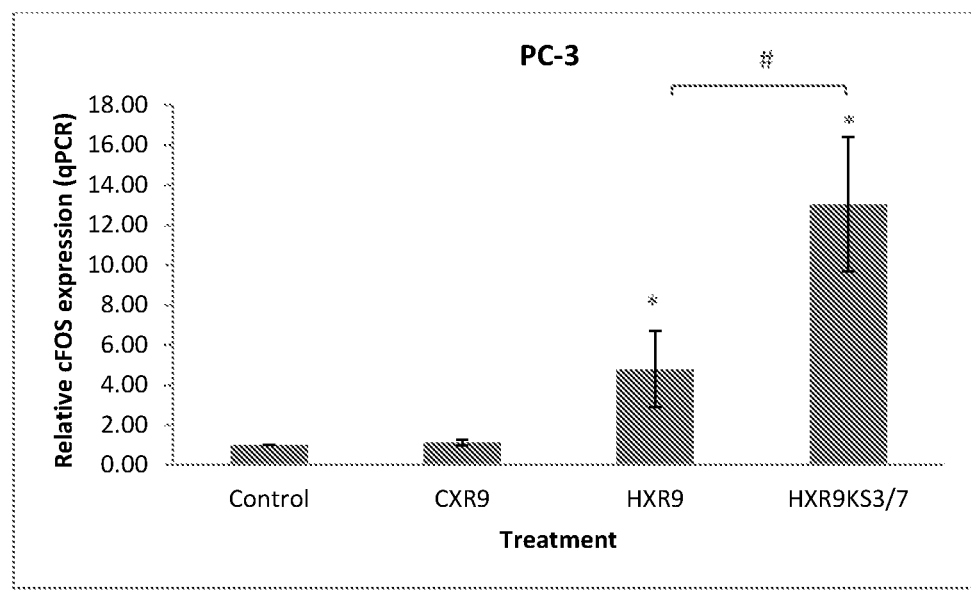

Figure 4: Annexin V-FITC assay (for apoptosis)
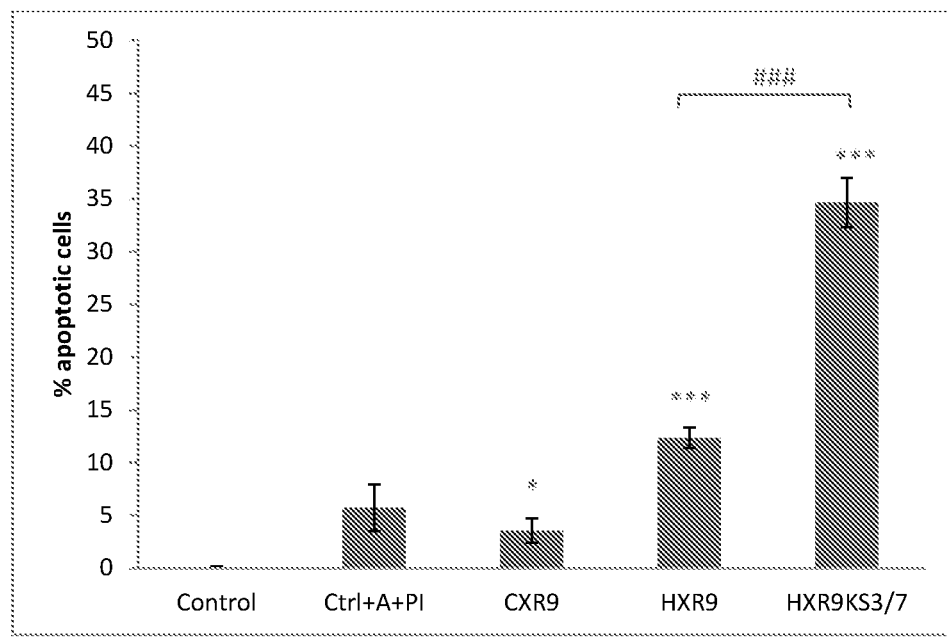

Figure 5: Mean relative tumour volume treated with HXR9KS3/7 (HTL001) relative to PBS injected mice as a function of time
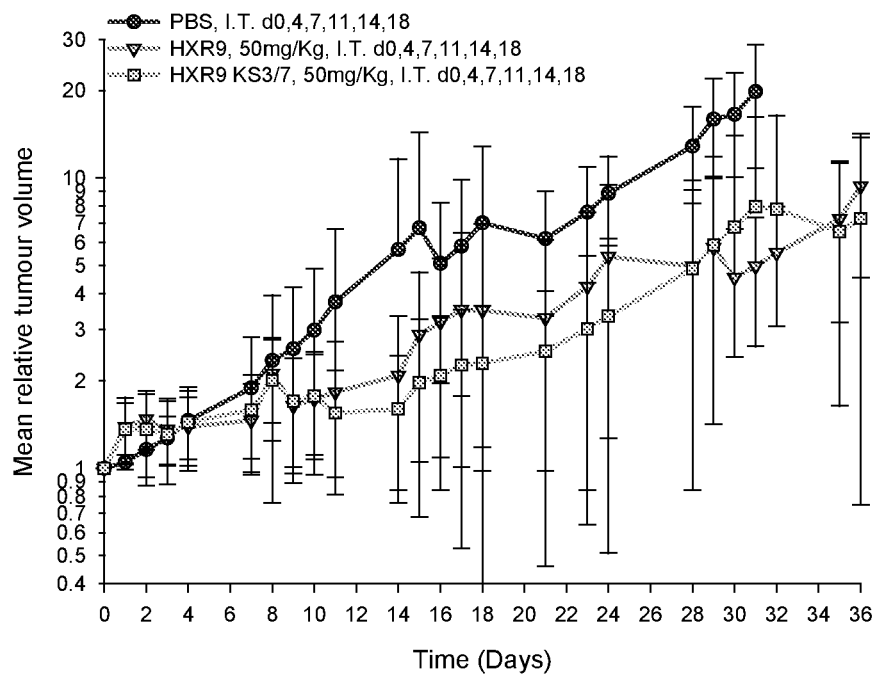

Figure 6: Mean relative % bodyweight of tumour bearing mice treated with HXR9KS3/7 (HTL001) relative to PBS injected mice as a function of time
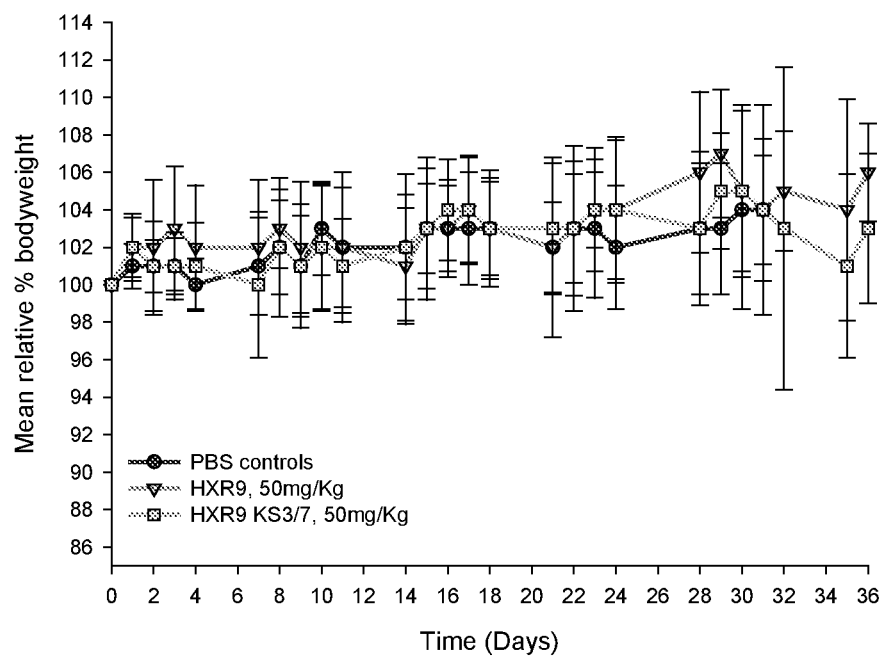

Figure 7: Time to tumor doubling and tripling, relative to PBS injected mice
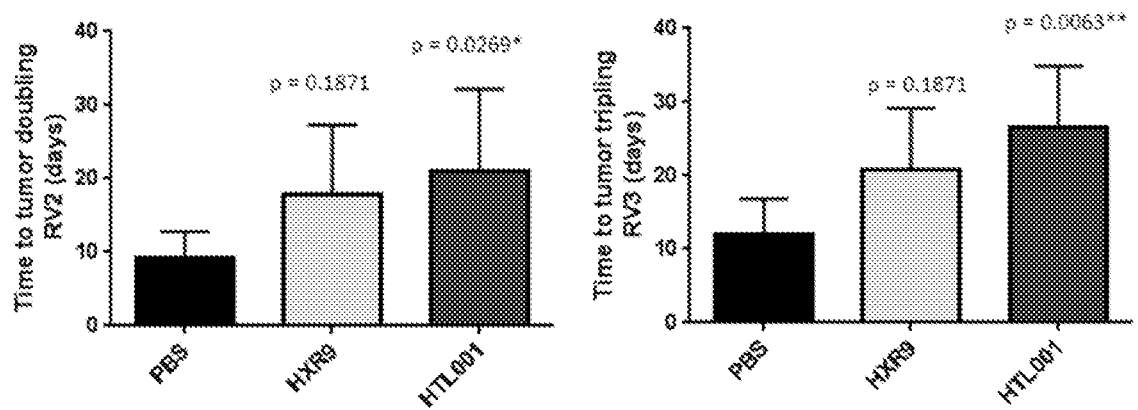

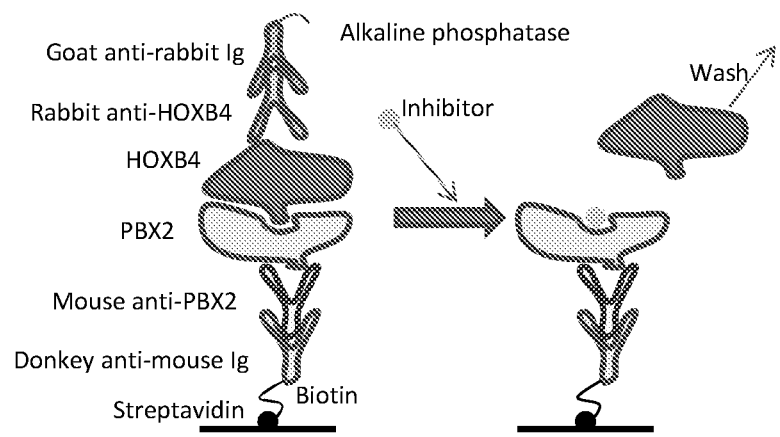
Figure 8: Schematic for HOXB4/PBX2 dimer assay

Figure 9: Expression of DUSP1 protein in PC3 cell line tumour xenografts
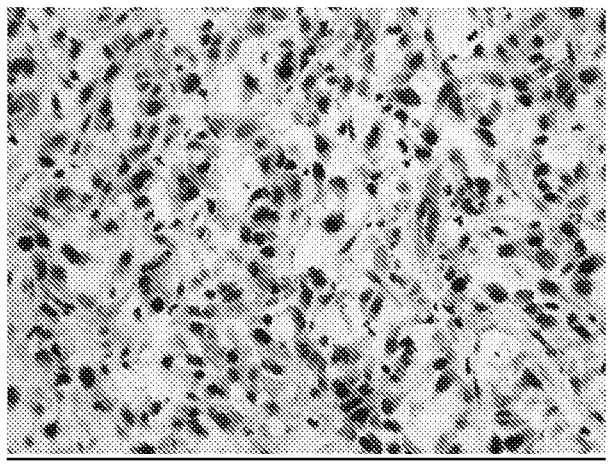
Figure 9a: Expression of DUSP1 protein in PBS injected PC3 cell line tumour xenografts.
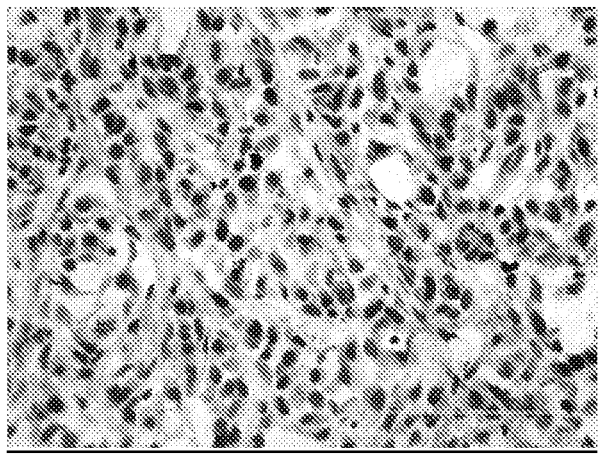
Figure 9b: Expression of DUSP1 protein in HXR9 treated PC3 cell line tumour xenografts.

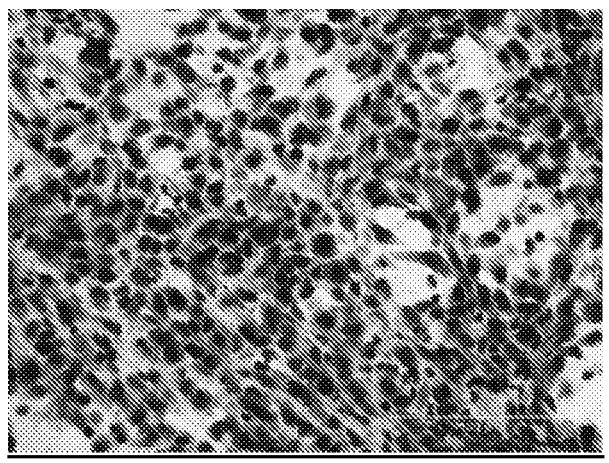
*Figure 9c: Expression of DUSP1 protein in HTL001 treated PC3 cell line tumour xenografts.*

PEPTIDES

CROSS-REFERENCE TO RELATED APPLICATIONS

This patent application is the U.S. national stage of International Patent Application No. PCT/GB2016/053282, filed on Oct. 20, 2016, which claims the benefit of Great Britain Patent Application No. 1518700.8, filed Oct. 21, 2015, the disclosures of which are incorporated herein by reference in their entireties for all purposes.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 22,985 Byte ASCII (Text) file named "pctgb2016053282-seq1-2nd" created on Feb. 1, 2019.

The present invention relates to novel peptides which impair PBX-dependent transcription regulation, particularly which affect the binding of HOX to PBX and their use in a number of applications, including the reduction of aberrant cell division, e.g. to treat certain cancers, and to maintain pluripotency of stem cells, e.g. to maintain the pluripotency of stem cells during culture expansion.

A variety of transcription factors are involved in the regulation of expression of proteins during embryogenesis and adult stem cell maturation. Homeobox (HOX) genes contain a highly conserved nucleotide sequence of about 180 bp which encodes a homeodomain of about 60 amino acids. A homeodomain is a DNA-binding protein domain which can bind to target sequences in other genes and regulate their expression during development. The clustered Hox genes are key developmental regulators and are highly conserved throughout evolution. The homeotic HOX proteins which they encode function as transcription factors to control axial patterning by regulating the transcription of subordinate downstream genes, e.g. developmental genes. Pre-B-cell transformation related gene (PBX) is also an important regulatory protein that controls gene expression during development by interacting cooperatively with HOX to bind to the target DNA (Mann et al., 1996, Trends Genet., 12(7), p 258-262).

It is known that by inhibiting the binding of PBX to its binding partners, aberrant cell growth may be reduced to prevent or treat disorders or conditions in which such cell growth occurs. Such inhibition has been found to have profound and useful effects on stem cells, which allows the pluripotency of these cells to be maintained. These findings offer significant clinical applications in which desired cells may be protected and possibly expanded whilst the growth of detrimental cells may be prevented (Morgan, R., Pirard, P. M., Shears, L., Sohal, J., Pettengell, R. & Pandha, H. S. (2007) Antagonism of HOX/PBX dimer formation blocks the in vivo proliferation of melanoma. Cancer Res, 67, 5806-5813; Shears, L., Plowright, L., Harrington, K., Pandha, H. S. & Morgan, R. (2008) Disrupting the interaction between HOX and PBX causes necrotic and apoptotic cell death in the renal cancer lines CaKi-2 and 769-P. J Urol, 180, 2196-2201; Plowright, L., Harrington, K. J., Pandha, H. S. & Morgan, R. (2009) HOX transcription factors are potential therapeutic targets in non-small-cell lung cancer (targeting HOX genes in lung cancer). Br J Cancer, 100, 470-475; Daniels, T. R., Neacato, II, Rodriguez, J. A., Pandha, H. S., Morgan, R. & Penichet, M. L. (2010) Disruption of HOX activity leads to cell death that can be enhanced by the interference of iron uptake in malignant B cells. Leukemia, 24, 1555-1565; Morgan, R., Plowright, L., Harrington, K. J., Michael, A. & Pandha, H. S. (2010) Targeting HOX and PBX transcription factors in ovarian cancer. BMC Cancer, 10, 89; Morgan, R., Boxall, A., Harrington, K. J., Simpson, G. R., Gillett, C., Michael, A. & Pandha, H. S. (2012) Targeting the HOX/PBX dimer in breast cancer. Breast Cancer Res Treat, 136, 389-398; Errico, M. C., Felicetti, F., Bottero, L., Mattia, G., Boe, A., Felli, N., Petrini, M., Bellenghi, M., Pandha, H. S., Calvaruso, M., Tripodo, C., Colombo, M. P., Morgan, R. & Care, A. (2013) The abrogation of the HOXB7/PBX2 complex induces apoptosis in melanoma through the miR-221&222-c-FOS pathway. Int J Cancer, 133, 879-892; Morgan, R., Boxall, A., Harrington, K. J., Simpson, G. R., Michael, A. & Pandha, H. S. (2014) Targeting HOX transcription factors in prostate cancer. BMC Urol, 14, 17; the contents of which are incorporated in their entirety for all purposes).

The present invention provides novel peptides, which impair PBX-dependent transcription regulation (e.g. activation or repression), e.g. by interfering with the interaction between PBX and its co-factors, preferably HOX, and its target DNA, e.g. which affect the binding of HOX and PBX proteins, have downstream effects which can offer great advantages such as preventing or reducing aberrant cell division and maintaining pluripotency of stem cells. In particular, the present invention provides novel peptides which act as PBX modulators, in particular antagonists, more particularly, of the binding of the hexapeptide region of HOX protein to PBX.

In one aspect, the invention provides a peptide comprising, or consisting of, the amino acid sequence of formula (I):

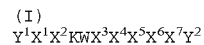

or a functionally equivalent derivative, variant or fragment thereof which may optionally be substituted, e.g. with a label or attachment moiety,
wherein
the sequence $X^1$ to $X^7$ is an amino acid sequence comprising at least 7 amino acids, which may optionally be interrupted by one or two amino acid residues between one or more of the 9 amino acid positions defined herein;
$X^1$ is selected from W, T, PE, KQI, VV, PQT, H, RI and absent;
$X^2$ is an amino acid with an aromatic side chain or cysteine;
$X^3$ is a hydrophobic amino acid
$X^4$ is an amino acid with a charged side chain;
$X^5$ is an amino acid with a basic side chain;
$X^6$ is an amino acid or absent;
$X^7$ is one or more amino acids or absent; and
$Y^1$ and $Y^2$ are each either absent or a peptide comprising a cationic polymer of basic amino acids, provided that at least one of $Y^1$ and $Y^2$ is present.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

A skilled person will appreciate that when two or more amino acids combine to form a peptide, the elements of water are removed, and what remains of each amino acid is called an amino-acid residue. The amino acid residue is the part of an amino acid that makes it unique from all the others. As such, reference herein to an 'amino acid' in the context of an amino acid sequence contained within a peptide will be understood to refer to the respective amino acid residue as appropriate.

"Peptides" as referred to herein are molecules with less than 100 amino acid residues; in particular less than 50 residues in length; more particularly less than 30 residues in length; more particularly from 10 to 25 residues in length.

Attachment of such a PBX modulator peptide to a cationic polymer of basic amino acids, such as a polyarginine sequence, may result in improved effectiveness. In particular, by using such a cationic polymer as a cell penetration moiety, the effects of the peptide may be seen much more rapidly than when other cell penetration sequences are used.

In one embodiment, $X^1$ is selected from W, T, PE, KQI, VV, PQT, H and RI. In a further embodiment $X^1$ is W.

In one embodiment, $X^2$ is selected from C, Y, F and W. In a further embodiment $X^2$ is Y.

In one embodiment, $X^3$ is selected from M, I, V and L. In a further embodiment, $X^2$ is M.

In one embodiment, $X^4$ is selected from K, D, R and H. In a further embodiment, $X^4$ is selected from K, D and R. In a further embodiment, $X^4$ is K or R. In a yet further embodiment, $X^4$ is K.

In one embodiment, $X^5$ is K or R. In a further embodiment, $X^5$ is K.

In one embodiment, $X^6$ is selected from K, R, E, H, D, N, Q, S, T and A. In a further embodiment, $X^6$ is H or A. In a yet further embodiment, $X^6$ is A. In an alternative embodiment, $X^6$ is absent.

In one embodiment, $X^7$ is selected from K, R, E, H, D, N, Q, S, T, A and G. In a further embodiment, $X^7$ is H, HR, A, AR or G. In a yet further embodiment, $X^7$ is H or A. In a yet further embodiment, $X^7$ is A. In an alternative embodiment, $X^7$ is absent.

In one embodiment, $Y^1$ and $Y^2$ are each either absent or a peptide comprising a cationic homopolymer of basic amino acids, such that at least one of $Y^1$ and $Y^2$ is present. In a further embodiment, the basic amino acids of $Y^1$ and $Y^2$ if present are selected from arginine.

In one embodiment, $Y^1$ and/or $Y^2$ acts as a cell penetration moiety or comprises a sequence which acts as a cell penetration moiety.

Suitably, the $Y^1$ and/or $Y^2$ moiety acts as a cell penetration moiety to allow or assist the entry of the peptide into a cell.

Suitably, the $X^1$ to $X^7$ sequence corresponds to the sequence capable of interfering with the interaction between HOX and PBX in vivo.

The peptide of the invention comprises or consists of any of the sequences $X^1$ to $X^7$ described herein, attached to any of the peptides $Y^1$ and/or $Y^2$ described herein. That is, any cationic polymer of basic amino acids described herein may be used in combination with any $X^1$ to $X^7$ sequence described herein, and may be located at the C-terminal, at the N-terminal, or at both termini of the peptide $X^1$ to $X^7$.

In the above sequence (I), $X^1$ to $X^4$ forms the hexapeptide sequence.

In one embodiment, peptides of formula (I) have the formula:

$$Y^1WYKWMKKHHY^2 \quad \text{(SEQ ID NO: 3)}$$

or functionally equivalent derivatives, variants or fragments thereof, wherein $Y^1$ and $Y^2$ are as defined herein.

The sequence $X^1$ to $X^7$ may be WYKWMKKHH (SEQ ID NO: 10) or WYKWMKKHHR (SEQ ID NO: 11), or $X^1$ to $X^7$ may be a variant of the sequence WYKWMKKHH (SEQ ID NO: 10), for example a variant wherein one, two, three, four or more amino acids are varied within the constraints of formula (I) above. For example, W at position $X^1$, may be absent, or may be replaced with any one selected from T, PE, KQI, VV, PQT, H and RI; Y at position $X^2$ may be replaced by another amino acid with an aromatic side chain or cysteine, in particular selected from C, F and W, more particularly C; $X^3$ may be replaced by another hydrophobic amino acid, in particular selected from L, I and V; K at position $X^4$ may be replaced by another amino acid with a charged side chain, in particular selected from D, R and H, more particularly R; K at position $X^5$ may be replaced by another amino acid with a basic side chain, in particular R; H at position $X^6$ may be replaced by another amino acid, in particular selected from K, R, E, D, N, Q, S and T, more particularly T; H at position $X^7$ may be replaced by any other one or more amino acids or may be absent, for example $X^7$ may be T or absent. Any one, two, three, four, five, six, or seven of these substitutions may be carried out to create an alternative peptide falling within the scope of formula (I) above.

In another embodiment, peptides of formula (I) have the formula:

$$Y^1WYKWMKKAAY^2 \quad \text{(SEQ ID NO: 4)}$$

or functionally equivalent derivatives, variants or fragments thereof, wherein $Y^1$ and $Y^2$ are as defined herein.

The sequence $X^1$ to $X^7$ may be WYKWMKKAA (SEQ ID NO: 12) or WYKWMKKAAR (SEQ ID NO: 13), or $X^1$ to $X^7$ may be a variant of the sequence WYKWMKKAA (SEQ ID NO: 12), for example a variant wherein one, two, three, four or more amino acids are varied within the constraints of formula (I) above. For example, W at position $X^1$, may be absent, or may be replaced with any one selected from T, PE, KQI, VV, PQT, H and RI; Y at position $X^2$ may be replaced by another amino acid with an aromatic side chain or cysteine, in particular selected from C, F and W, more particularly C; $X^3$ may be replaced by another hydrophobic amino acid, in particular selected from L, I and V; K at position $X^4$ may be replaced by another amino acid with a charged side chain, in particular selected from D, R and H, more particularly R; K at position $X^5$ may be replaced by another amino acid with a basic side chain, in particular R; A at position $X^6$ may be replaced by another amino acid, in particular selected from K, R, E, D, N, Q, S and T, more particularly T; A at position $X^7$ may be replaced by any other one or more amino acids or may be absent, for example $X^7$ may be T or absent. Any one, two, three, four, five, six, or seven of these substitutions may be carried out to create an alternative peptide falling within the scope of formula (I) above.

In another embodiment, peptides of formula (I) have the formula:

$$Y^1WYKWMKKY^2 \quad \text{(SEQ ID NO: 5)}$$

or functionally equivalent derivatives, variants or fragments thereof, wherein $Y^1$ and $Y^2$ are as defined herein.

The sequence $X^1$ to $X^7$ may be WYKWMKK (SEQ ID NO: 14) or WYKWMKKR (SEQ ID NO: 15), or $X^1$ to $X^5$ may be a variant of the sequence WYKWMKK (SEQ ID NO: 14), for example a variant wherein one, two, three, four or more amino acids are varied within the constraints of formula (I) above. For example, W at position $X^1$, may be absent, or may be replaced with any one selected from T, PE, KQI, VV, PQT, H and RI; Y at position $X^2$ may be replaced by another amino acid with an aromatic side chain or cysteine, in particular selected from C, F and W, more particularly C; $X^3$ may be replaced by another hydrophobic amino acid, in particular selected from L, I and V; K at position $X^4$ may be replaced by another amino acid with a charged side chain, in particular selected from D, R and H, more particularly R; K at position $X^5$ may be replaced by another amino acid with a basic side chain, in particular R. Any one, two, three, four, or five of these substitutions may be carried out to create an alternative peptide falling within the scope of formula (I) above.

In one embodiment, amino acid substitutions occur at positions $X^2$, and $X^3$ to $X^7$. In a further embodiment, amino acid substitutions occur at one, two, three or four of positions $X^3$ to $X^7$.

For example, in one embodiment, residues $X^1$ to $X^7$ in formula (I) above may be:
$X^1$=W; $X^2$=Y or C; $X^3$=M, I, V or L; $X^4$=K, R or D; $X^5$=K or R; $X^6$=H; A, T or absent;
$X^7$=any amino acid or absent;
$X^1$=W; $X^2$=Y or C; $X^3$=M, I, V or L; $X^4$=K, R or D; $X^5$=K or R; $X^6$=H, A, T or absent;
$X^7$=H, HR, A, AR, T, G or absent;
$X^1$=W; $X^2$=Y; $X^3$=M, I, V or L; $X^4$=K or R; $X^5$=K or R; $X^6$=H, A, T or absent; $X^7$=any amino acid or absent;
$X^1$=W; $X^2$=Y; $X^3$=M, I, V or L; $X^4$=K or R; $X^5$=K or R; $X^6$=H, A or T; $X^7$=H, HR, A, AR, T, G or absent.

Suitable sequences for $X^1$ to $X^7$ include:

WYKWMKKHH (SEQ ID NO: 10)
WCKWLDRHG (SEQ ID NO: 19)
WYKWVKKHH (SEQ ID NO: 20)
WYKWIKKHH (SEQ ID NO: 21)
WYKWMRKHH (SEQ ID NO: 22)
WYKWMKRHH (SEQ ID NO: 23)
WYKWMRRHH (SEQ ID NO: 24)
WYKWMKKTH (SEQ ID NO: 25)
WYKWMKKHT (SEQ ID NO: 26)
WYKWMKKTT (SEQ ID NO: 27)
WCKWMKKHH (SEQ ID NO: 28)
WCKWMRKHH (SEQ ID NO: 29)
WCKWMKRHH (SEQ ID NO: 37)
WCKWMRRHH (SEQ ID NO: 38)
WYKWMKRTH (SEQ ID NO: 39)
WYKWMRKTH (SEQ ID NO: 40)
WYKWMRRTH (SEQ ID NO: 41)
WYKWMRKHT (SEQ ID NO: 42)
WYKWMKRHT (SEQ ID NO: 43)
WYKWMRRHT (SEQ ID NO: 44)
WYKWMRRTT (SEQ ID NO: 45)
WYKWLRKHH (SEQ ID NO: 46)
WYKWLKRHH (SEQ ID NO: 47)
WYKWMKKH (SEQ ID NO: 48)
WYKWMKKAA (SEQ ID NO: 12)
WCKWLDRAG (SEQ ID NO: 49)
WYKWVKKAA (SEQ ID NO: 50)
WYKWIKKAA (SEQ ID NO: 51)
WYKWMRKAA (SEQ ID NO: 52)
WYKWMKRAA (SEQ ID NO: 53)
WYKWMRRAA (SEQ ID NO: 54)
WYKWMKKTA (SEQ ID NO: 55)
WYKWMKKAT (SEQ ID NO: 56)
WCKWMKKAA (SEQ ID NO: 57)
WCKWMRKAA (SEQ ID NO: 58)
WCKWMKRAA (SEQ ID NO: 59)
WCKWMRRAA (SEQ ID NO: 60)
WYKWMKRTA (SEQ ID NO: 61)
WYKWMRKTA (SEQ ID NO: 62)

```
                                     (SEQ ID NO: 63)
WYKWMRRTA (SEQ ID NO: 64)
WYKWMRKAT (SEQ ID NO: 65)
WYKWMKRAT (SEQ ID NO: 66)
WYKWMRRAT (SEQ ID NO: 67)
WYKWLRKAA (SEQ ID NO: 68)
WYKWLKRAA (SEQ ID NO: 69)
WYKWMKKA (SEQ ID NO: 14)
WYKWMKK
```

Any of these variant $X^1$-$X^7$ sequences may be used in combination with any of the $Y^1$ and/or $Y^2$ residues described herein. For example, any of the $X^1$-$X^7$ sequences described herein may be used with a $(Arg)_{6-12}$ peptide, for example an $(Arg)_6$ [SEQ ID NO:90], $(Arg)_7$ [SEQ ID NO:91], $(Arg)_8$ [SEQ ID NO:92], $(Arg)_9$[SEQ ID NO:9], $(Arg)_{10}$ [SEQ ID NO:93], $(Arg)_{11}$ [SEQ ID NO:1] or $(Arg)_{12}$ [SEQ ID NO:2] peptide attached at the C-terminal, at the N-terminal or at both ends.

As explained above, $Y^1$ and/or $Y^2$ is, or comprises, a cationic polymer of basic amino acids. Typically, $Y^1$ and/or $Y^2$ comprise a sequence capable of acting as a cell penetration moiety.

In one embodiment, $Y^1$ is attached via the N-terminal amino group on $X^1$. In an alternative embodiment, $Y^1$ is attached via a side chain of $X^1$. In one embodiment, $Y^2$ is attached via the C-terminal carboxyl group on $X^7$. In an alternative embodiment, $Y^2$ is attached via a side chain of $X^7$. Where present, $Y^1$ and $Y^2$ are each suitably a peptide of 50 amino acids or less which is optionally substituted.

As used herein a "cell penetration moiety" refers to a molecule, structure or collection of molecules which assist or facilitate entry of the molecule to which it is attached into a cell.

In the context of $Y^1$ and/or $Y^2$, any cationic polymer of basic amino acids that can allow or help a molecule, such as a peptide to which it is attached, to enter a cell may be used. The moiety may be a generally acting substance that can enter a variety of cell types, or may be specific or targeted to a particular cell type to be treated.

A cell penetration moiety may be directly linked to the peptide $X^1$ to $X^7$, or may be attached via a linker sequence of one or more amino acids. The linker sequence may comprise the amino acid(s) at position $X^7$. Typically, the linker comprises amino acids that do not have bulky side groups and therefore do not obstruct the folding of the protein such as serine and glycine. The linker permits the cell penetration moiety to assist or facilitate entry of the peptide into a cell and also allows the HOX-PBX interacting part of the peptide to interfere with HOX-PBX binding. The linker may be a flexible amino acid linker. The linker typically has a length of up to 20 amino acids, such as 5 to 18 or 10 to 16, in particular 15 amino acids.

A cell penetration moiety may alternatively be associated with a peptide $X^1$ to $X^7$, e.g. may encapsulate or form a complex with said peptide, e.g. by using liposomes for lipofection or polycations or cationic lipids. "Associated with" as used herein refers to the moiety being attached to, or connected in some way, to the peptide.

In one embodiment $Y^1$ and/or $Y^2$ is, or comprises, a cationic polymer or a pharmaceutically acceptable salt thereof.

As used herein, the term "pharmaceutically acceptable salts" refers to salts that retain the biological effectiveness and properties of the compounds of this invention and, which typically are not biologically or otherwise undesirable. The peptides of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate, trifluoroacetate and trifluoromethylsulfonate salts.

Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, trifluoromethylsulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

Furthermore, the peptides of the present invention, including their salts, can also be obtained in the form of their hydrates, or include other solvents used for their crystallization.

Peptides of the invention, i.e. peptides of formula (I) that contain groups capable of acting as donors and/or acceptors for hydrogen bonds may be capable of forming co-crystals with suitable co-crystal formers. These co-crystals may be prepared from peptides of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a peptide of formula (I).

A skilled person will appreciate that when both a basic group and an acid group are present, the peptides of the present invention may also form internal salts, e.g., zwitterions.

$Y^1$ and/or $Y^2$ is, or comprises a cationic polymer of basic amino acids. Suitably the basic amino acids are selected from lysine, arginine and histidine. Such polyamino acids are readily available from Sigma-Aldrich.

$Y^1$ and/or $Y^2$ may be, or may comprise, a homopolymer of a basic amino acid. For example, $Y^1$ and/or $Y^2$ may be a polyarginine, polylysine or polyhistidine. Alternatively the polyamino acid may be a polymer of one or more basic amino acids, optionally also including one or more non-basic amino acids. Thus the polyamino acid may comprise one or more basic amino acids and optionally one or more other amino acids. Such a copolymer typically comprises a majority of basic amino acids. For example, 50 to 100% of the amino acids in the copolymer may be basic. Suitably, 60 to 90% or 70 to 80% are basic. In one embodiment at least 75%, for instance at least 85%, 95%, 98%, or 99% of the amino acids in the copolymer are basic. In one embodiment, these basic amino acids, or a group of such basic amino acids, may be located together as a chain of only basic amino acids within the copolymer. In general, the basic amino acids comprise one or more of lysine, histidine and arginine. Where the copolymer includes one or more non-basic amino acids, these are preferably not acidic amino acids, such as aspartate or glutamate. The one or more non-basic amino acids may include amino acids with aliphatic or aromatic side chains, for example, threonine, proline, tryptophan, serine or phenylalanine.

The amino acids in any of the above polyamino acids may be L or D amino acids.

In one embodiment, the polyamine is a homopolymer of arginine $(Arg)_x$ or lysine $(Lys)_x$. Poly-L-arginine or poly-L-lysine are suitable, in particular poly-L-arginine. Typically, the homopolymer has a molecular weight of from about 500 to 15000, for example from 500 to 10000, from 500 to 5000, or from 500 to 1000. In one embodiment, x in the above formula may range from 3 to 100, for example from 3 to 50, from 3 to 30 or 3 to 20.

Small peptide homopolymers are particularly suitable, for example, those having a molecular weight in the range 500 to 1500, such as 500 to 1250, or 700 to 1000. Typically, in a small peptide, x has a value of from 3 to 15, for example from 6 to 12. For example, $Y^1$ and/or $Y^2$ may be, or comprise, a polyarginine consisting of between 6 and 12 arginine residues. Exemplified herein are peptides wherein $Y^1$ and/or $Y^2$ is $(Arg)_9$, e.g. where $Y^1$ is absent and $Y^2$ is Arg-Arg-Arg-Arg-Arg-Arg-Arg-Arg-Arg (SEQ ID NO: 9).

Particularly suitable peptides thus include those wherein $Y^1$ and/or $Y^2=(Arg)_9$.

Particularly suitable peptides have the sequence

```
WYKWMKKHHRRRRRRRRR;        (SEQ ID NO: 6)

WYKWMKKAARRRRRRRRR;        (SEQ ID NO: 7)

WYKWMKKRRRRRRRRR;          (SEQ ID NO: 8)
``` or a functionally equivalent derivative, variant or fragment thereof.

The amino acids in the peptides of formula (I) may be L or D amino acids.

All the amino acids in the peptide may have the same stereochemistry, for example, the peptide may consist of only L-amino acids or only D-amino acids. Alternatively, the peptide may comprise a combination of both L- and D-amino acids. As explained below, by varying the number and position of L- and D-amino acids in the peptide, it may be possible to effect the stability of the resultant peptide, for example, the stability of the peptide after administration to the body. In one embodiment at least the N-terminal- and C-terminal-most amino acids of the peptide are in the D-conformation while the remaining amino acids are in the L-conformation.

Optionally one, two, three, four or more further amino acids are also in the D conformation. Optionally one or more amino acids at, or adjacent to position $X^7$ are in the D-conformation. Optionally the amino acids at positions $X^2$ to $X^3$ are in the L-conformation.

It is known that the stability of PBX modulator peptides may be improved by incorporating one or more D-amino acids in the peptide. In particular, the half life of the peptides in plasma may be improved by using D amino acids in at least the N- and C-terminal positions of the peptide. This improved half life is seen in peptides which comprise a variety of cell penetration sequences.

Accordingly, in a second embodiment, a peptide of the invention comprises or consists the amino acid sequence of formula (II):

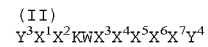

(II)
$Y^3X^1X^2KWX^3X^4X^5X^6X^7Y^4$ wherein
the sequence $X^1$ to $X^7$ is an amino acid sequence comprising at least 7 amino acids, which may optionally be interrupted by one or two amino acid residues between one or more of the 9 amino acid positions defined herein;
$X^1$ is selected from W, T, PE, KQI, VV, PQT, H, RI and absent;
$X^2$ is an amino acid with an aromatic side chain or cysteine;
$X^3$ is a hydrophobic amino acid
$X^4$ is an amino acid with a charged side chain;
$X^5$ is an amino acid with a basic side chain;
$X^6$ is an amino acid or absent;
$X^7$ is one or more amino acids or absent; and
$Y^3$ and $Y^4$ are each either absent or a peptide comprising a sequence comprising a cell penetration moiety, provided that at least one of $Y^3$ and $Y^4$ is present;
wherein at least the N-terminal and C-terminal amino acids of said peptide are in the D-conformation;
or a functionally equivalent derivative, variant or fragment thereof.

In one embodiment, $X^1$ is selected from W, T, PE, KQI, VV, PQT, H and RI. In a further embodiment $X^1$ is W.

In one embodiment, $X^2$ is selected from C, Y, F and W. In a further embodiment $X^2$ is Y.

In one embodiment, $X^3$ is selected from M, I, V and L. In a further embodiment, $X^2$ is M.

In one embodiment, $X^4$ is selected from K, D, R and H. In a further embodiment, $X^4$ is selected from K, D and R. In a further embodiment, $X^4$ is K or R. In a yet further embodiment, $X^4$ is K.

In one embodiment, $X^5$ is K or R. In a further embodiment, $X^5$ is K.

In one embodiment, $X^6$ is selected from K, R, E, H, D, N, Q, S, T and A. In a further embodiment, $X^6$ is H or A. In a yet further embodiment, $X^6$ is A. In an alternative embodiment, $X^6$ is absent.

In one embodiment, $X^7$ is selected from K, R, E, H, D, N, Q, S, T, A and G. In a further embodiment, $X^7$ is H, A or G. In a yet further embodiment, $X^7$ is H or A. In a yet further embodiment, $X^7$ is A. In an alternative embodiment, $X^7$ is absent.

In the above sequence, $X^1$ to $X^4$ forms the hexapeptide sequence.

In one embodiment, peptides of formula (II) have the formula:

$$Y^3WYKWMKKHHY^4 \quad \text{(SEQ ID NO: 16)}$$

or functionally equivalent derivatives, variants or fragments thereof, wherein $Y^3$ and $Y^4$ are as defined herein.

The sequence $X^1$ to $X^7$ may be WYKWMKKHH (SEQ ID NO: 10) or WYKWMKKHHR (SEQ ID NO: 11), or $X^1$ to $X^7$ may be a variant of the sequence WYKWMKKHH (SEQ ID NO: 10), for example a variant wherein one, two, three, four or more amino acids are varied within the constraints of formula (I) above. For example, W at position $X^1$, may be absent, or may be replaced with any one selected from T, PE, KQI, VV, PQT, H and RI; Y at position $X^2$ may be replaced by another amino acid with an aromatic side chain or cysteine, in particular selected from C, F and W, more particularly C; $X^3$ may be replaced by another hydrophobic amino acid, in particular selected from L, I and V; K at position $X^4$ may be replaced by another amino acid with a charged side chain, in particular selected from D, R and H, more particularly R; K at position $X^5$ may be replaced by another amino acid with a basic side chain, in particular R; H at position $X^6$ may be replaced by another amino acid, in particular selected from K, R, E, D, N, Q, S and T, more particularly T; H at position $X^7$ may be replaced by any other one or more amino acids or may be absent, for example $X^7$ may be T or absent. Any one, two, three, four, five, six, or seven of these substitutions may be carried out to create an alternative peptide falling within the scope of formula (II) above.

In another embodiment, peptides of formula (II) have the formula:

$$Y^3WYKWMKKAAY^4 \quad \text{(SEQ ID NO: 17)}$$

or functionally equivalent derivatives, variants or fragments thereof, wherein $Y^3$ and $Y^4$ are as defined herein.

The sequence $X^1$ to $X^7$ may be WYKWMKKAA (SEQ ID NO: 12) or WYKWMKKAAR (SEQ ID NO: 13), or $X^1$ to $X^7$ may be a variant of the sequence WYKWMKKAA (SEQ ID NO: 12), for example a variant wherein one, two, three, four or more amino acids are varied within the constraints of formula (II) above. For example, W at position $X^1$, may be absent, or may be replaced with any one selected from T, PE, KQI, VV, PQT, H and RI; Y at position $X^2$ may be replaced by another amino acid with an aromatic side chain or cysteine, in particular selected from C, F and W, more particularly C; $X^3$ may be replaced by another hydrophobic amino acid, in particular selected from L, I and V; K at position $X^4$ may be replaced by another amino acid with a charged side chain, in particular selected from D, R and H, more particularly R; K at position $X^5$ may be replaced by another amino acid with a basic side chain, in particular R; A at position $X^6$ may be replaced by another amino acid, in particular selected from K, R, E, D, N, Q, S and T, more particularly T; A at position $X^7$ may be replaced by any other one or more amino acids or may be absent, for example $X^7$ may be T or absent. Any one, two, three, four, five, six, or seven of these substitutions may be carried out to create an alternative peptide falling within the scope of formula (II) above.

In another embodiment, peptides of formula (II) have the formula:

$$Y^3WYKWMKKY^4 \quad \text{(SEQ ID NO: 18)}$$

or functionally equivalent derivatives, variants or fragments thereof, wherein $Y^3$ and $Y^4$ are as defined herein.

The sequence $X^1$ to $X^7$ may be WYKWMKK (SEQ ID NO: 14) or WYKWMKKR (SEQ ID NO: 15), or $X^1$ to $X^5$ may be a variant of the sequence WYKWMKK (SEQ ID NO: 14), for example a variant wherein one, two, three, four or more amino acids are varied within the constraints of formula (II) above. For example, W at position $X^1$, may be absent, or may be replaced with any one selected from T, PE, KQI, VV, PQT, H and RI; Y at position $X^2$ may be replaced by another amino acid with an aromatic side chain or cysteine, in particular selected from C, F and W, more particularly C; $X^3$ may be replaced by another hydrophobic amino acid, in particular selected from L, I and V; K at position $X^4$ may be replaced by another amino acid with a charged side chain, in particular selected from D, R and H, more particularly R; K at position $X^5$ may be replaced by another amino acid with a basic side chain, in particular R. Any one, two, three, four, or five of these substitutions may be carried out to create an alternative peptide falling within the scope of formula (II) above.

In one embodiment, amino acid substitutions occur at positions $X^2$, and $X^3$ to $X^7$. In a further embodiment, amino acid substitutions occur at one, two, three or four of positions $X^3$ to $X^7$.

For example, in one embodiment, residues $X^1$ to $X^7$ in formula (II) above may be:

$X^1$=W; $X^2$=Y or C; $X^3$=M, I, V or L; $X^4$=K, R or D; $X^5$=K or R; $X^6$=H, A, T or absent;
$X^7$=any amino acid or absent;
$X^1$=W; $X^2$=Y or C; $X^3$=M, I, V or L; $X^4$=K, R or D; $X^5$=K or R; $X^6$=H, A, T or absent;
$X^7$=H, HR, A, AR, T, G or absent;
$X^1$=W; $X^2$=Y; $X^3$=M, I, V or L; $X^4$=K or R; $X^5$=K or R; $X^6$=H, A, T or absent; $X^7$=any amino acid or absent;
$X^1$=W; $X^2$=Y; $X^3$=M, I, V or L; $X^4$=K or R; $X^5$=K or R; $X^6$=H, A, T; $X^7$=H, HR, A, AR, T, G or absent.

Any of these variant $X^1$-$X^7$ sequences may be used in combination with any of the $Y^3$ and/or $Y^4$ residues described herein. For example, any of the $X^1$-$X^7$ sequences described herein may be used with a $(Arg)_{6-12}$ peptide, for example an $(Arg)_7$, $(Arg)_8$ or $(Arg)_9$ peptide attached at the C-terminal, at the N-terminal or at both ends. Alternatively, any of the $X^1$-$X^7$ sequences described herein may be used with a penetratin peptide, such as those described below, attached at the C-terminal, at the N-terminal or at both ends.

As defined hereinabove a "cell penetration moiety" refers to a molecule, structure or collection of molecules which assist or facilitate entry of the molecule to which it is attached into a cell.

A variety of such moieties are well-known in the art and include peptides such as penetratins, tat-derived proteins, peptide signal sequences that allow cell entry, peptides comprising such peptide signals as well as synthetic and/or chimeric cell-penetrating peptides such as transportan or model amphipathic peptides (Lindgren et al., 2000, TiPS, 21, p 99-103 and Derossi et al., 1998, Trends C. Biol., 8, p 84-87). Non-peptide molecules or substances which are capable of entering cells may also be used. Suitably, the cell penetration moiety acts by a receptor-independent mechanism. Any substance that can allow or help a molecule, such as a peptide of the invention, to enter a cell may be used. The moiety may be a generally acting substance that can enter a variety of cell types, or may be specific or targeted to a particular cell type to be treated.

A cell penetration moiety may be directly linked to the peptide $X^1$ to $X^7$, or may be attached via a linker sequence of one or more amino acids. The linker sequence may comprise the amino acid(s) at position $X^7$. A cell penetration moiety may alternatively be associated with a peptide $X^1$ to $X^7$, e.g. may encapsulate or form a complex with said peptide, e.g. by using liposomes for lipofection or polycations or cationic lipids.

"Associated with" as used herein refers to the moiety being attached to, or connected in some way, to the peptide.

In one embodiment, $Y^3$ and/or $Y^4$ may comprise or consist of a cationic polymer of basic amino acids as described above. Any such cationic polymer described hereinabove may be used in this embodiment of the invention. For example, $Y^3$ and/or $Y^4$ may comprise or consist of a polyarginine sequence such as $(Arg)_9$.

In an alternative embodiment said cell penetration moiety comprises or consists of a peptide based on the penetratin sequence having the following general formula (SEQ ID NO: 30)

wherein
$X^9$ is R or Q or absent;
$X^{10}$, $X^{12}$ are each independently I or L; and
$X^{11}$, $X^{14}$, $X^{15}$, $X^{16}$ and $X^{17}$ are each independently K or R.
Suitably the penetratin sequence has the form:

QIKIWFQNRRMKWKK; (SEQ ID NO: 70)

QIRIWFQNRRMKWKK; (SEQ ID NO: 71)

QIKIWFQNKRMKWKK; (SEQ ID NO: 72)

QIKIWFQNKKMKWKK; (SEQ ID NO: 73)

QIRIWFQNRKMKWKK; (SEQ ID NO: 74)

QIRIWFQNRRMRWKK; (SEQ ID NO: 75)

QIRIWFQNRRMKWRK; (SEQ ID NO: 76)

QIRIWFQNRRMKWKR; (SEQ ID NO: 77)

QIRIWFQNRRMKWRR; (SEQ ID NO: 78)

QIRIWFQNRRMKWKK; (SEQ ID NO: 79)

QIKIWFQNRRMKWRK; (SEQ ID NO: 80)

QIRIWFQNKRMKWRK; (SEQ ID NO: 81)

QIKLWFQNRRMKWKK; (SEQ ID NO: 82)

QLKLWFQNRRMKWKK; (SEQ ID NO: 83)
or

QLRIWFQNRRMKWKK. (SEQ ID NO: 84)

A particularly suitable peptide has the sequence

WYKWMKKHHRQIKIWFQNRRMKWKK (SEQ ID NO: 31)

or a functionally equivalent derivative, variant or fragment thereof.

An alternative peptide has the sequence WYKWMK-KHHRQIKIWFQNRRMKWK (SEQ ID NO: 34).

A particularly suitable peptide has the sequence

WYKWMKKAARQIKIWFQNRRMKWKK (SEQ ID NO: 32)

An alternative peptide has the sequence WYKWMK-KAARQIKIWFQNRRMKWK (SEQ ID NO: 35).

A particularly suitable peptide has the sequence

WYKWMKKRQIKIWFQNRRMKWKK (SEQ ID NO: 33)

An alternative peptide has the sequence WYKWMK-KRQIKIWFQNRRMKWK (SEQ ID NO: 36).

In peptides of formula (II), two or more of the amino acids are present in the D conformation. At least the N-terminal and C-terminal amino acids are present in the D-conformation. One, two, three, four, five or more further amino acids may also be D amino acids. For example, the amino acid(s) at or adjacent to position $X^7$ may be or comprise D-amino acid(s). All the amino acids in the peptide may be in the D-conformation. In one embodiment the N- and C-terminal amino acids are D-amino acids and the remaining amino acids are L-amino acids. Optionally, the amino acids at positions $X^2$ to $X^3$ are in the L conformation. In one embodiment, at least the N- and C terminal amino acids are D-amino acids, and the amino acids at positions $X^2$ to $X^3$ are L amino acids.

"Functionally equivalent" derivatives, variants or fragments thereof refers to peptides related to, or derived from, the peptides of the invention where the amino acid sequence has been modified by, for example, the use of modified amino acids or by single or multiple amino acid (e.g. at 1 to 10, e.g. 1 to 5, in particular 1 or 2 residues) substitution, addition and/or deletion but which nonetheless retain functional activity. For example functionally equivalent derivatives of the specific peptides of SEQ ID NOs: 6, 7, 8, 31, 32 and 33, may retain the ability to act as HOX mimics and thus antagonize the interaction between HOX proteins and PBX proteins (in particular PBX1 or PBX2). Such an interaction may be assessed using common laboratory techniques. One such method is set out in International patent application PCT/GB2006/002390 published as WO2007/00601 4 Jan. 2007, the contents of which are incorporated in their entirety for all purposes. Functionally equivalent derivatives of the $(Arg)_x$ sequence or a penetratin sequence may retain activity as a cell penetration moiety, for example by allowing entry of the attached peptide into a cell. Such an ability may also be assessed by commonly known techniques, such as those described in Example 1.

Suitable functionally equivalent derivatives, variants or fragments of the peptides of SEQ ID Nos: 6, 7 or 8 will fall within the scope of or comprise formula (I). Suitable functionally equivalent derivatives, variants or fragments of $(Arg)_9$ will fall within the scope of $Y^1$ and/or $Y^2$ as described above.

Suitable functionally equivalent derivatives, variants or fragments of the peptides of SEQ ID Nos: 31, 32 or 33 will fall within the scope of or comprise formula (II). Suitable functionally equivalent derivatives, variants or fragments of the penetratin sequence will fall within the scope of or comprise the sequence of SEQ ID NO:30.

Within the meaning of "addition", variants are included which are amino and/or carboxyl terminal fusion proteins or polypeptides, comprising an additional protein or polypeptide fused to the peptide sequence.

As mentioned above, the peptide may be substituted, preferably at the N- or C-terminus, by a further moiety. Such moieties may be added to aid the function of the peptide, its targeting or its synthesis, capture or identification, e.g. a label (e.g. biotin) or lipid molecules. Such moieties may alternatively be found within the peptide itself. For example a moiety such as a label may be attached to an amino acid located internally within the peptide. For example, $X^7$ may comprise all or part of such a moiety, or said moiety may form part of, or be located within, $Y^2$, $Y^3$ and/or $Y^4$.

"Substitution" variants preferably involve the replacement of one or more amino acids with the same number of amino acids and making conservative amino acid substitutions. For example, an amino acid may be substituted with an alternative amino acid having similar properties, for example, another basic amino acid, another charged amino acid, another hydrophilic amino acid or another aliphatic amino acid. Some properties of the main amino acids are as follows in Table 1:

TABLE 1

| Properties of the 20 main amino acids | |
|---|---|
| Ala (A) | aliphatic, hydrophobic, neutral |
| Cys (C) | polar, hydrophobic, neutral |
| Asp (D) | polar, hydrophilic, charged (−) |
| Glu (E) | polar, hydrophilic, charged (−) |
| Phe (F) | aromatic, hydrophobic, neutral |
| Gly (G) | aliphatic, neutral |
| His (H) | aromatic, polar, hydrophilic charged (+) |
| Ile (I) | aliphatic, hydrophobic, neutral |
| Lys (K) | polar, hydrophilic, charged (+) |
| Leu (L) | aliphatic, hydrophobic, neutral |
| Met (M) | hydrophobic, neutral |
| Asn (N) | polar, hydrophilic, neutral |
| Pro (P) | hydrophobic, neutral |
| Gln (Q) | polar, hydrophilic, neutral |
| Arg (R) | polar, hydrophilic, charged (+) |
| Ser (S) | polar, hydrophilic, neutral |
| Thr (T) | polar, hydrophilic, neutral |
| Val (V) | aliphatic, hydrophobic, neutral |

TABLE 1-continued

| Properties of the 20 main amino acids | |
|---|---|
| Trp (W) | aromatic, hydrophobic, neutral |
| Tyr (Y) | aromatic, polar, hydrophobic |

Suitably, "derivatives" or "variants" include those in which instead of the naturally occurring amino acid the amino acid which appears in the sequence is a structural analog thereof. Amino acids used in the sequences may also be derivatized or modified, e.g. labelled, providing the function of the peptide is not significantly adversely affected.

Derivatives and variants as described above may be prepared during synthesis of the peptide or by post-production modification, or when the peptide is in recombinant form using the known techniques of site-directed mutagenesis, random mutagenesis, or enzymatic cleavage and/or ligation of nucleic acids.

Functionally-equivalent "fragments" according to the invention may be made by truncation, e.g. by removal of one or more amino acids from the N and/or C terminal ends. Such fragments may be derived from formula (I) or (II) or may be derived from a functionally equivalent peptide as described above. Suitably such fragments are between 6 and 30 residues in length, e.g. 6 to 25 or 10 to 15 residues.

Suitably, functional variants according to the invention have an amino acid sequence which has more than 70%, e.g. 75 or 80%, preferably more than 85%, e.g. more than 90 or 95% homology to, for example, SEQ ID NO: 6, 7, 8, 31, 32 or 33, (according to the test described hereinafter).

In connection with amino acid sequences, "sequence identity" refers to sequences which have the stated value when assessed using ClustalW (Thompson et al., 1994, supra) with the following parameters:

Pairwise alignment parameters-Method: accurate, Matrix: PAM, Gap open penalty: 10.00, Gap extension penalty: 0.10;

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatized.

Peptides of the invention, as defined herein, may be chemically modified, for example, post-translationally modified. For example they may be glycosylated or comprise modified amino acid residues. They can be in a variety of forms of polypeptide derivatives, including amides and conjugates with polypeptides.

Chemically modified peptides also include those having one or more residues chemically derivatized by reaction of a functional side group. Such derivatized side groups include those which have been derivatized to form amine hydrochlorides, p-toluene sulfonyl groups, carbobenzoxy groups, t-butyloxycarbonyl groups, chloroacetyl groups and formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzyl histidine.

Also included as chemically modified peptides are cyclised peptides, i.e. peptides of the invention which are linked with a covalent bond to generate a ring. Typically an amino terminus and a carboxy terminus (so called head-totail cyclisation), an amino terminus and a sidechain (so called head-to-sidechain cyclisation), carboxy terminus and a sidechain (so called sidechain-to-tail cyclisation), or a side chain and a side chain (so called sidechain-to-sidechain cyclisation) may be linked with a covalent bond to form a cyclic peptide. Head-to-tail cyclic peptides may typically be formed by amide bond formation. Sidechain-to-sidechain cycles may typically be formed via Cys-Cys disulfide bridge formation or amide bond formation within a cyclic peptide. Alternatively, an amino terminus, a carboxy terminus or a side chain may be linked with a covalent bond to the peptide backbone to form a cyclic peptide.

Also included as chemically modified peptides are those which contain one or more naturally occurring amino acid derivatives of the twenty standard amino acids. For example, 4-hydroxyproline may be substituted for proline or homoserine may be substituted for serine.

A peptide of the invention may carry a revealing label. Suitable labels include radioisotopes, fluorescent labels, enzyme labels, or other protein labels such as biotin.

Any formula given herein is also intended to represent unlabeled forms as well as isotopically labeled forms of the peptides. Isotopically labeled peptides have structures depicted by the formulas given herein except that one or more atoms are replaced by an atom having a selected atomic mass or mass number. Examples of isotopes that can be incorporated into peptides of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled peptides as defined herein, for example those into which radioactive isotopes, such as $^3H$, and $^{14}C$, are present. Such isotopically labelled peptides are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled peptides may be particularly desirable for PET or SPECT studies. Isotopically labeled peptides of this invention and prodrugs thereof can generally be prepared by carrying out the procedures disclosed in the schemes or in the examples and preparations described below by substituting a readily available isotopically labeled reagent for a non-isotopically labeled reagent.

Isotopically-labeled peptides of the invention can generally be prepared by conventional techniques known to those skilled in the art or by processes analogous to those described herein using an appropriate isotopically-labeled reagents in place of the non-labeled reagent previously employed.

Pharmaceutically acceptable solvates in accordance with the invention include those wherein the solvent of crystallization may be isotopically substituted, e.g. D20, d6-acetone, $d_6$-DMSO.

Peptides as described above for use in accordance with the invention may be prepared by conventional modes of synthesis including genetic or chemical means.

Synthetic techniques, such as a solid-phase Merrifield-type synthesis, may be preferred for reasons of purity, antigenic specificity, freedom from unwanted side products and ease of production. Suitable techniques for solid-phase peptide synthesis are well known to those skilled in the art (see for example, Merrifield et al., 1969, Adv. Enzymol 32, 221-96 and Fields et al., 1990, Int. J. Peptide Protein Res, 35, 161-214). Chemical synthesis may be performed by methods well known in the art involving cyclic sets of reactions of selective deprotection of the functional groups of a terminal amino acid and coupling of selectively protected amino acid residues, followed finally by complete deprotection of all functional groups.

Synthesis may be performed in solution or on a solid support using suitable solid phases known in the art.

Since the peptides of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

In an alternative embodiment a peptide of the invention may be produced from or delivered in the form of a polynucleotide which encodes, and is capable of expressing, it. Such polynucleotides can be synthesised according to methods well known in the art, as described by way of example in Sambrook et al (1989, Molecular Cloning—a laboratory manual; Cold Spring Harbor Press). Such polynucleotides may be used in vitro or in vivo in the production of a peptide of the invention. Such polynucleotides may therefore be administered or used in the treatment of cancer or another disease or condition as described herein.

The present invention also includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al (ibid).

Thus, the peptide may be provided by delivering such a vector to a cell and allowing transcription from the vector to occur. Suitably, a polynucleotide of the invention or for use in the invention in a vector is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

The vectors may be for example, plasmid, virus or phage vectors provided with an origin of replication, optionally a promoter for the expression of the said polynucleotide and optionally a regulator of the promoter. The vectors may contain one or more selectable marker genes, for example an ampicillin resistence gene in the case of a bacterial plasmid or a resistance gene for a fungal vector. Vectors may be used in vitro, for example for the production of DNA or RNA or used to transfect or transform a host cell, for example, a mammalian host cell. The vectors may also be adapted to be used in vivo, for example to allow in vivo expression of the polypeptide.

Promoters and other expression regulation signals may be selected to be compatible with the host cell for which expression is designed. For example, yeast promoters include *S. cerevisiae* GAL4 and ADH promoters, *S. pombe* nmt1 and adh promoter. Mammalian promoters, such as b-actin promoters, may be used. Tissue-specific promoters are especially preferred. Mammalian promoters include the metallothionein promoter which can be induced in response to heavy metals such as cadmium. Viral promoters may also be used, for example the SV40 large T antigen promoter, adenovirus promoters, the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSY IE promoters), or HPV promoters, particularly the HPV upstream regulatory region (URR). All these promoters are readily available in the art.

The invention also includes cells that have been modified to express a peptide of the invention. Such cells include transient, or preferably stable higher eukaryotic cell lines, such as mammalian cells or insect cells, lower eukaryotic cells, such as yeast or prokaryotic cells such as bacterial cells. Particular examples of cells which may be modified by insertion of vectors encoding for a peptide of the invention include mammalian HEK293T, CHO, HeLa and COS cells. Suitably the cell line selected will be one which is not only stable, but also allows for mature glycosylation and cell surface expression of a polypeptide. Expression may be achieved in transformed oocytes. A suitable peptide may be expressed in cells of a transgenic non-human animal, in particular a mouse. A transgenic non-human animal expressing a peptide of the invention is included within the scope of the invention. A peptide of the invention may also be expressed in *Xenopus laevis* oocytes or melanophores.

The present invention also extends to antibodies (monoclonal or polyclonal) and their antigen-binding fragments (e.g. F(ab)2, Fab and Fv fragments i.e. fragments of the "variable" region of the antibody, which comprises the antigen binding site) directed to peptides as defined hereinbefore, i.e. which bind to epitopes present on the peptides and thus bind selectively and specifically to such peptides, and which may be used in the methods of the invention.

The peptides of the invention, as described above, are able to specifically block the interaction between PBX and HOX. Peptides of the invention may ablate or reduce the proliferation of a range of cancer cell types. Accompanying these changes, down-regulation of a number of known HOX targets may be observed. As described in more detail below, the peptides of the invention may therefore have therapeutic uses in the treatment of cancers in which Hox genes are expressed, as cytoprotective agents during other cancer therapies or in the ex vivo protection of stem cell cultures.

Peptides described above may be used to block interactions of PBX with its binding partners, e.g. HOX, and preferably thereby prevent the binding of HOX to its target DNA. Thus in a further aspect the present invention provides use of a peptide as described herein to reduce or inhibit binding of PBX to a binding partner, in particular HOX, or the use of such peptides to reduce or inhibit binding of HOX to its target DNA.

"PBX" refers to the protein products of the family of pre-B-cell transformation related genes and includes genes encoding extradenticle homeoprotein proteins and homologues of the Drosophila extradenticle gene, such as genes in vertebrates. Vertebrate PBX proteins are transcription factors that contain a homeodomain (Mann et al., 1996).

"HOX" refers to protein products of the homeobox genes which contain a sequence which encodes a homeodomain of about 60 amino acids and a sequence which encodes the hexapeptide sequence N-terminal to the homeodomain (Morgan et al., 2000, TIG, 16(2), p 66-67 and Krumlauf, 1994, Cell, 78(2), p 191-201). The HOX proteins are transcription factors that act to define anterior-posterior development in early development. Such PBX or HOX genes or proteins as described herein include homologues present in any multicellular animal, but are suitably from vertebrates, e.g. from mammals, in particular from humans.

As referred to herein "binding" refers to the interaction or association of at least two moieties in a reversible or irreversible reaction, wherein said binding is suitably specific and selective.

As used herein a "binding partner" refers to a molecule which recognizes and binds specifically (i.e. in preference to binding to other molecules) to its binding partner. Such binding pairs when bound together form a complex.

A "reduction in binding" refers to a decrease in binding, e.g. as manifest by an increased concentration of one of the binding pair required to achieve binding. Reduction includes a slight decrease as well as absolute abrogation of specific binding. A total reduction of specific binding is considered to equate to a prevention of binding.

"Inhibition" refers to competitive interference of the binding of the binding partners by the peptide, which serves to reduce the partners' binding.

Agents which prevent or reduce PBX-dependent transcription regulation, have been found to have advantageous effects on aberrant cell division (International patent application PCT/GB2003/005425 published as WO2004/055049 1 Jul. 2004 and International patent application PCT/GB2006/002390 published as WO2007/00601 4 Jan. 2007, the contents of which are incorporated in their entirety for all purposes).

Such agents are typically those which prevent, reduce or inhibit the binding of PBX to its binding partners, in particular the binding between PBX and HOX (such as antagonists of the interaction between HOX and PBX, e.g. the peptides described hereinabove). However, suitable agents also include those that affect binding of the transcription factors to the target DNA, e.g. which block the interaction of PBX or its binding partner, such as HOX, to the target DNA. Suitably, such agents prevent HOX-dependent transcription regulation.

Whilst not wishing to be bound by theory, it is believed that antagonists of HOX:PBX binding prevent the interaction between multiple important HOX:PBX protein binding partners, and the HOX proteins are therefore unable to act as transcription factors on the genes to which they bind. The failure to regulate expression of these genes may have numerous effects on the cells, for example reducing or preventing the excessive cell division and inducing cell death. Similarly, any moiety which prevents or reduces PBX-dependent transcription regulation, e.g. blocks the interaction of HOX with its target DNA, may be expected to have similar effects.

Agents which are suitable for this purpose include antagonists of the interaction between HOX and/or PBX and the DNA target to which they bind, antagonists of the interaction between PBX and its binding partners, typically HOX proteins, or agents which impair the binding ability of HOX/PBX or the target DNA, e.g. which block relevant sites or cause structural changes at relevant sites on HOX/PBX or the target DNA or reduce the number of molecules available for binding (which may be achieved by for example modifying the expression/expressed product of PBX/HOX). Suitably however, antagonists are employed. Suitable agents are the peptides of the invention as described above.

In a further aspect, therefore, the present invention provides a method of reducing aberrant cell division wherein said cells are administered a peptide of the invention, hereinafter alternately referred to as "agent of the invention" which prevents or reduces PBX-dependent transcription regulation, suitably which reduces or prevents binding of PBX to a binding partner, preferably to HOX (suitably HOXB4, HOXB8 or HOXA9) or reduces or prevents binding of HOX to its target DNA, suitably an antagonist, suitably an antagonist of the interaction between HOX and PBX, and which suitably inhibits HOX-dependent transcription regulation.

As described herein, "aberrant cell division" refers to cell division above the normal level (i.e. abnormal cell division) considered appropriate under the conditions which exist. Markers of aberrant cell division are well known to the person skilled in the art and can be used to determine whether a particular cell has been affected. For example, cells undergoing aberrant cell division may show atypical cytology, for example cellular pleomorphism, nuclear pleomorphism, nuclear hyperchromatism or an increased nuclear cytoplasmic ratio. Cells undergoing aberrant cell division may show a failure of cell differentiation. More particularly, such aberrant cell division may be present in certain conditions or diseases/disorders as described hereinafter, such as a cancer.

"Reducing" cell division refers to reducing the rate of cell growth. Suitably, cell growth is reduced to less than 0.5, in particular less than 0.25, e.g. less than 0.1 relative to control growth (without the agent) over the same time period (wherein control growth=1). Suitably, reduced cell division encompasses cell death/lack of viability which may occur in addition, or as an alternative to the reduction in cell growth. When cell death occurs suitably more than 50% of the existing cells, in particular more than 75% of the cells, are destroyed.

By adjusting the dose of the agent used it may also be possible to completely ablate some malignancies. Peptides of the invention may therefore be used to slow the growth of, or completely destroy, cancerous cells. As explained in more detail below, a suitable dose will depend on a number of factors and can be determined by a skilled practitioner.

As described herein "PBX-dependent transcription regulation" refers to activation or suppression of the transcription of genes by processes in which PBX plays a pivotal role, e.g. acts as a cofactor in the transcription regulatory complexes.

Prevention or reduction refers to a measurable change in the extent of transcription. Prevention equates to a reduction in transcription to undetectable levels.

"Target DNA" refers to the gene containing the regulatory region to which PBX, HOX or any member of the transcription regulation complex containing such proteins, binds.

As referred to herein, an "antagonist" is a molecule or complex of molecules which by virtue of structural similarity to one molecule of a binding pair competes with that molecule for binding to the other molecule of the binding pair.

As specifically referred to herein, the antagonists of the invention are antagonists of the interaction between HOX and PBX which prevent or reduce binding between those entities. Suitable antagonists bind to, or compete with the binding site on HOX or PBX. Typically antagonists compete by mimicking the PBX binding site on HOX, i.e. binding to PBX.

Such methods may be performed in vitro, in vivo or ex vivo.

Having regard to their ability to specifically block the interaction between PBX and HOX and inhibit aberrant cellular division, the peptides of the invention, hereinafter alternately referred to as "agents of the invention", are useful in the treatment or prevention of a condition or disorder in which aberrant cell division occurs, particularly a cancer Treatment in accordance with the invention may be symptomatic or prophylactic, Thus in a further aspect the invention includes an agent of the invention for use as a pharmaceutical.

Therefore according to a further aspect, the invention provides an agent of the invention for treating or preventing a condition or disorder in which aberrant cell division occurs.

Therefore according to a further aspect, the invention provides the use of an agent of the invention in the manufacture of a medicament for the prevention or treatment of a condition or disorder in which aberrant cell division occurs.

Therefore according to a further aspect, the invention provides a method for preventing or treating a condition or disorder in which aberrant cell division which comprises administering to a subject in need thereof a therapeutically effective amount of an agent of the invention.

In accordance with the foregoing, the invention also provides as a further aspect a method for preventing or treating a condition or disorder in which aberrant cell division occurs, particularly cancer, which comprises administering to a subject, particularly a human subject, in need thereof a therapeutically effective amount of an agent of the invention.

In another aspect the invention provides an agent of the invention for preventing or treating a condition or disorder in which aberrant cell division occurs, particularly cancer.

In another aspect the invention provides the use of an agent of the invention in the manufacture of a medicament for the prevention or treatment of a condition or disorder in which aberrant cell division occurs, particularly cancer.

As referred to herein a "disorder" or a "disease" refers to an underlying pathological disturbance in a symptomatic or asymptomatic organism relative to a normal organism, which may result, for example, from infection or an acquired or congenital genetic imperfection.

A "condition" refers to a state of the mind or body of an organism which has not occurred through disease, e.g. the presence of a moiety in the body such as a toxin, drug or pollutant.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder. For example, symptoms which may be affected include tumour size or numbers of cancerous cells in a given sample (or reduced stem cell numbers as described hereinafter).

"Prevention" of a condition or disorder refers to delaying or preventing the onset of a condition or disorder or reducing its severity, as assessed by the appearance or extent of one or more symptoms of said condition or disorder.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, a subject is "in need of" a treatment if such subject would benefit biologically, medically or in quality of life from such treatment.

The term "a therapeutically effective amount" of an agent of the invention refers to an amount of the agent of the invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the agent of the invention that, when administered to a subject, is effective to at least partially alleviating, inhibiting, preventing and/or ameliorating a condition or disorder in which aberrant cell division occurs. In another non-limiting embodiment, the term "a therapeutically effective amount" refers to the amount of the agent of the invention that, when administered to a cell, or a tissue, or a non-cellular biological material, or a medium, is effective to at least partially reducing aberrant cell division.

As an alternative to performing the methods in vivo, such methods may be performed in vitro, e.g. to reduce the cell division of, or eliminate, cells undergoing aberrant cell growth, in a sample. Appropriate culture conditions are as described for other methods of the invention as described hereinafter.

This is particularly useful in cell samples containing both normal and aberrant cells in which aberrant cells may be controlled/removed and the sample containing the normal cells used for subsequent procedures, e.g. returned to the donor body. This may be useful to, for example, eliminate aberrant haematopoietic blood cells from a blood sample of a patient, e.g. leukaemic cells, and the remaining cells may then be returned to the body of that patient.

Thus in a yet further aspect the present invention provides a method of reducing aberrant cell division (in particular of reducing the growth, more particularly involving the death and hence reducing the number, of cancer cells) in cells in a sample, wherein an agent of the invention as described hereinbefore is administered to said sample. In a method for treating patients suffering from a disorder or condition typified by aberrant cell division (or preventing the same), said sample may be harvested from said patient and then returned to that patient as described hereinafter. In this context, a "sample" refers to any material obtained from a human or non-human animal, including embryonic, foetal, immature and adult stages of said animal, which contains cells undergoing aberrant cell division and include tissues and body fluids.

"Body fluids" in this case include in particular blood, spinal fluid and lymph and "tissues" include tissue obtained by surgery or other means.

Suitably, the aberrant cell division occurs in cells from eukaryotic organisms which may be any eukaryotic organisms such as human beings, other mammals and animals, birds, insects and fish.

Non-human animals from which cells may be derived or on which methods of the invention may be conducted include, but are not limited to mammals, particularly primates, domestic animals, livestock and laboratory animals. Thus animals include mice, rats, chickens, frogs, guinea pigs, cats, dogs, pigs, cows, goats, sheep, horses. Suitably, the cells are derived from, and the methods used to treat, or be prophylactic in, humans.

In particular, the cells undergoing aberrant cell division are cancer cells and the disorder to be treated or prevented is a cancer. Cancers that can be treated in this way are those cancers which involve the expression of HOX and PBX genes, wherein HOX/PBX dimer expression is reduced by the activity of a peptide of the invention, thus blocking the growth of, reducing the proliferation of, or leading directly to the death of, the cancerous cells.

In a further embodiment, the peptide of the invention may act on the cancerous cells to move them from a quiescent state into the cell cycle and thus make them more susceptible to other, e.g. cytotoxic, anti-cancer treatments.

Suitably said cell to be treated expresses one or more Hox genes. For example, said cell may express one or more of HOXA1, HOXA3, HOXA4, HOXA5, HOXA7, HOXA9, HOXB1, HOXB2, HOXB3, HOXB4, HOXB8, HOXB9, HOXC4, HOXC6, HOXC8, HOXD3, HOXD4, HOXD8, and HOXD9. Said cell may express one or more of HOXB4, HOXB8 and HOXA9. It is possible that the level of Hox gene expression in the cell may be directly related to the sensitivity of the cell to the peptides of the invention. The peptides of the invention would therefore be more effective at treating cells which show high levels of HOX gene expression, for example higher levels of HOX gene expression than that in the surrounding tissue or higher levels of HOX gene expression than that of other cancer types where the cell is a cancer cell. The methods of the invention may therefore be particularly suitable where the cells to be treated show such increased or higher levels of HOX gene expression.

Suitably said cancers are malignant or pre-malignant or benign tumours and include carcinomas, sarcomas, gliomas, melanomas and lymphomas, including cancers of the bladder, kidney, pancreas, brain, head and neck, breast, gut, prostate, lung and ovary and leukaemias and lymphomas. In particular, colorectal, pancreatic, bladder, prostate, cervical, ovarian, gastric and non-small cell lung cancers.

A condition or disorder characterised by aberrant cell division is a cancer, including, but not limited to, mesothelioma, hepatobilliary (hepatic and billiary duct), a primary or secondary CNS tumor, a primary or secondary brain tumor, lung cancer (NSCLC and SCLC), bone cancer, pancreatic cancer, melanoma and non-melanomatous skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), gastrointestinal stromal tumor, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cartilidge, or bone, cancer of the urethra, cancer of the penis, prostate cancer, testicular cancer, testicular lymphoma, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In one embodiment of the present invention the cancer is lung cancer (NSCLC and SCLC), melanoma, cancer of the head or neck, ovarian cancer, colon cancer, rectal cancer, cancer of the anal region, stomach cancer, breast cancer, cancer of the kidney or ureter, renal cell carcinoma, carcinoma of the renal pelvis, cancer of the thyroid gland, cancer of the parathyroid gland, pancreatic cancer, prostate cancer, neoplasms of the central nervoussystem (CNS), primary CNS lymphoma, non hodgkins's lymphoma, or spinal axis tumors, or a combination of one or more of the foregoing cancers.

In a particular embodiment, the cancer is lung cancer (NSCLC and SCLC), melanoma, cancer of the head or neck, ovarian cancer, breast cancer, prostate cancer, colon cancer, or renal cell carcinoma.

In another embodiment, said condition or disorder in which aberrant cell division occurs is a benign proliferative disease, including, but not limited to, psoriasis, benign prostatic hypertrophy or restinosis.

In one embodiment, said condition or disorder in which aberrant cell division occurs is myelodysplasia (MDS).

In some cancers, for example some forms of human pre-B cell leukaemia, PBX may act as an oncogene. The effects of PBX in such cancers will be different to that in other cancer types where PBX is not an oncogene. The effects of a peptide of the invention may also therefore be different.

In one embodiment, therefore, the present invention does not apply to such cancers because the effect of a peptide of the invention will be via a different mechanism to the PBX:HOX effect described hereinabove. In this embodiment, therefore, a peptide of the invention may be used in the treatment or prevention of a cancer or other disorder in which aberrant cell division occurs, and in which PBX does not act as an oncogene. Suitably, the cancerous cells express one or more Hox genes. For example, a suitable cancer for treatment by a method of the invention may be a leukaemia other than human pre-B cell leukaemia.

In some cancers, such as acute myeloid leukaemia (AML), peptides of the invention may block the proliferation of the cancerous cells, but may also stimulate those cells to leave the G0/G1 quiescent state and enter the cell cycle. These two effects are seen in the same cells under the same conditions. This is likely to be due to the cells being triggered to leave G0/G1 by the peptide (i.e. enter the cell cycle) but then failing to divide and instead either differentiating or undergoing apoptosis. The peptides of the invention may be used in the treatment of both primary AML and mature myeloid leukaemias. This suggests a specific utility for the peptides of the invention in acute myeloid and lymphoid leukaemias. Blocking PBX/HOX interactions in these cells using a peptide of the invention may therefore form an effective treatment for preventing leukaemia cell growth in vivo. In addition, by increasing the proportion of leukaemic cells that enter the cell cycle, the peptides of the invention may also increase their sensitivity to other cancer treatments such as chemotherapy. The peptides of the invention may therefore be used in combination with another cancer treatment as described further below.

Agents which prevent or reduce PBX-dependent transcription regulation have also been found to have beneficial effects on stem cells.

"Stem cells" as referred to herein are undifferentiated cells which are capable of differentiating into various cells, e.g. various blood cell types, and include haematopoietic (e.g. found in the bone marrow) and neural and hepatic stem cells, embryonic stem cells and embryonic germ cells and encompass both pluri- and toti-potent cells. Embryonic cells are considered to be those cells derived from the inner cell mass of the blastocyst and embryonic germ cells are those cells isolated from the primordial germ cell of the gonadal ridge of the 5 to 10 week old foetus. Suitably, the cells are derived from eukaryotic organisms as described previously.

Prevention of PBX-mediated transcription regulation results in reduced, but continued, cell division and the appearance of molecular markers of differentiation (e.g. CD38). However on removal of the agent blocking that transcriptional regulation, cells reverted to stem cells as assessed by the appearance of molecular markers (e.g. HOXB4, HOXB8, HOXA9, AC133), thus reflecting pluripotency of the cells (International patent application PCT/GB2006/002390 published as WO2007/00601 4 Jan. 2007, the contents of which are incorporated in their entirety for all purposes). Whilst not wishing to be bound by theory, it is believed that despite the appearance of markers of differentiation/maturation, no phenotypic changes symptomatic of differentiation occur and the cells instead have a significantly reduced rate of cell cycling while the agent is being administered. On removal of the agent, the cells reverted to stem cells.

It is also believed that treatment of pluripotent haematopoietic stem and progenitor cells (HSPCs) with a peptide of the invention may block their proliferation, and increase the proportion of cells in the G0-G1 phase of the cell cycle. The longevity of the cultures confirms the effects of putative stem cells as well as more differentiated progenitor populations. The specificity of this inhibitory effect on these gene targets is underlined by its reversibility, with gene transcription and cell growth resuming on removal of the peptide.

These results have a number of applications which include maintenance or expansion of stem cells (e.g. in culture), for example for temporary storage of said cells, with possible expansion during that storage period. Such cells may then, for example, be used in clinical applications in which the addition of stem cells is desirable, e.g. to patients that have reduced numbers of stem cells and/or the ability to produce certain differentiated cell types, due to, for example, age, disease (e.g. cancers or autoimmune disease), congenital factors, environmental influences or contaminants and/or administered chemicals. In particular stem cells may be harvested from a patient prior to chemotherapy or radiotherapy and maintained and/or expanded and returned to that patient after chemotherapy or radiotherapy.

As an alternative example, the stem cells may be used to provide cells from which a particular differentiated cell may be formed, e.g. neuronal cells, particularly in adult recipients where such suitable stem cells are absent or only low levels are present. The recipient of the stem cells is suitably also the donor, but may also be a different individual. The peptides of the invention may therefore be used to protect explanted tissue that contains stem cells (e.g. bone marrow cells) during culture in vitro or ex vivo.

Cells may also be maintained ex vivo or in vivo, for example to maintain viability during treatment that might normally affect their viability, e.g. during chemo- or radiotherapy.

Agents as described herein, i.e. peptides of the invention, can be used to reduce the susceptibility of stem cells to damage by such treatments by temporarily stopping or slowing the cell cycle of the stem cells. For example, peptides of the invention may be used to reduce the side effects caused by other cancer treatments, e.g. cytotoxic shock associated with many chemotherapeutic regimes. The cytoprotective effect of peptides of the invention on stem cells in vivo may also allow higher levels or doses of such cancer treatments to be used due to the decreased side-effects produced. For example, a higher dose of chemo- or radio-therapy may be possible.

Thus in a further aspect, the present invention provides a method of maintaining or expanding stem cells, wherein said method comprises at least the step of contacting said cells with an agent of the invention as described hereinbefore, suitably an antagonist, suitably an antagonist of the interaction between HOX and PBX. This method may be used to maintain pluri- or toti-potency of the stem cells.

Suitably this method is performed in vitro or ex vivo, in culture, in which case the method may contain an initial step of harvesting stem cells from a donor. However, the method may also be used in vivo to maintain or improve the numbers of stem cells in an individual, particularly during exposure to agents or treatments that might cause stem cell damage. In such circumstances, the present invention provides a method of maintaining or expanding stems cells in a patient wherein said patient is administered an agent of the invention, suitably an antagonist, suitably an antagonist of the interaction between HOX and PBX.

"Maintaining" the cells refers to maintaining the viability of a large proportion of the starting, e.g. harvested, cells with minimal cell division, during the course of the treatment or culture period.

"Expanding" the cells refers to at least some cell division, suitably significant cell division, to increase the numbers of cells during the course of treatment, or culture.

As referred to herein "culture" refers to the growth or maintenance of the cells in a controlled artificial environment, i.e. ex vivo. Standard techniques for culture of cells are well known. Suitably cells are cultured at 37° C., 5% $CO_2$ in a humidified atmosphere in a standard culture medium. Suitably said culture is conducted for at least 2 hours, suitably more than 24 hours; e.g. between 24 hours and 8 weeks.

"Contacting" as used herein refers to any suitable technique which allows the agent to have access, and thus the possibility of binding, to cells in the sample, e.g. by application to the culture medium.

After the cells have been maintained or expanded, the agent may be removed to recover pluri- or toti-potency. When the method is performed in vivo this may be achieved by ceasing administration and allowing the body to clear the agent. In vitro or ex vivo, the agent is removed from the culture medium, e.g. by washing and replacement with fresh medium. Alternatively, the agent may be removed by allowing it to degrade naturally.

Thus the invention provides a method of maintaining or expanding stem cells and/or obtaining pluri- or toti-potent stem cells, in culture, suitably an expanded population of said cells, wherein said method comprises at least the steps of:

a) contacting said cells in culture with an agent of the invention, which reduces or prevents PBX dependent transcription regulation as described hereinabove, suitably an antagonist, suitably an antagonist of the interaction between HOX and PBX; b) culturing said cells in the absence of said agent.

It should be noted that the peptide becomes degraded within a few days during culture and thus active peptide is depleted. Thus, step b) may be performed without any prior washing if sufficient time has lapsed for degradation to occur. As mentioned previously, culture times are at least 2 hours, suitably more than 24 hours, e.g. between 24 hours and 8 weeks.

The method may contain an initial step of harvesting stem cells from a donor.

Cells obtained by this and other methods of the invention comprise further aspects of the invention as does their use as a medicament.

The cells thus prepared by the above described in vitro or ex vivo methods may then be administered to an individual in need of such stem cells. Optionally, the cells may be modified prior to transplant, e.g. during the course of culturing or just prior to transplanting, e.g. by genetic modification, e.g. for gene transfer or to import a function not previously present in said cells, e.g. to compensate for a genetic deficit, e.g. by providing a missing factor, e.g. adenosine deaminase (ADA).

Thus in a yet further aspect, the present invention provides a method of treating an individual in need of stem cells wherein stem cells prepared according to the above described method are administered to said individual.

Suitably said individual in need of said stem cells is an individual who has (or will have) lower than normal or desirable levels of such cells, which condition may exist normally, e.g. through age or as a result of external factors e.g. through chemotherapy or radiotherapy. Suitably, said stem cells are derived from the recipient individual.

Thus, the present invention provides a method of improving the number of stem cells in a recipient individual wherein said method comprises at least the steps of:

a) harvesting stem cells from a donor, b) culturing said stem cells according to the methods described hereinabove;

c) administering said cultured stem cells to said recipient individual.

Suitably, the method is a method of improving the number of stem cells in a patient subject to chemotherapy or radiotherapy, wherein said method comprises at least the steps of:

a) harvesting stem cells from said patient prior to chemotherapy or radiotherapy, b) culturing said stem cells according to the methods described hereinbefore;

c) administering said cultured stem cells to said patient after completion of chemotherapy or radiotherapy.

Alternatively, harvesting step a) in the methods above may be absent and step b) may comprise culturing stem cells harvested from the donor according to the methods described hereinbefore. Said cells may be harvested by obtaining a sample of cells, tissue or body fluid from said donor and optionally extracting the cells therefrom.

As used herein a "sample" refers to any material obtained from the donor, e.g. human or non-human animal, including embryonic, foetal, immature and adult stages of said animal, which contains stem cells and includes, tissues and body fluids.

"Body fluids" include blood and spinal fluid.

"Tissue samples" include tissue obtained by surgical interventions (e.g. bone marrow or liver) or by other means e.g. placenta and umbilical cord. The animals from which cells are derived or to which the methods are applied are preferably as described' hereinabove in connection with the methods of reducing aberrant cell division.

As used herein reference to "improving the number of stem cells" refers to increasing the number of stem cells to be added (suitably of the particular type to be added, e.g. haematopoietic stem cells) relative to the number present in the individual at the time at which administration would occur. Thus in the case of a patient subject to chemotherapy or radiotherapy the observed improvement is in the number of stem cells in a patient post-chemotherapy or post-radiotherapy. An improvement may also consist of the addition of certain stem cells previously absent or present in very low numbers, e.g. neuronal stem cells.

Alternatively, the present invention provides an agent of the invention for the treatment or prevention of conditions or disorders typified by a need for stem cells, suitably in treating or preventing conditions or disorders in which stem cell numbers are lower than normal, e.g. due to chemotherapy or radiotherapy, or in conditions in which the provision of stem cells may allow the production of one or more particular differentiated cells that are absent or present in abnormally low numbers, or lower numbers than desired, at the site of interest.

Conditions or disorders in which stem cell numbers are lower than normal include autoimmune disorders, radiotherapy, chemotherapy and certain viral infections.

Conditions in which the use of stem cells by transplantation may provide appropriate differentiated cells which are absent or present at lower than normal or lower than desired levels include Alzheimer's disease, Parkinson's disease and other age-related disorders or conditions (including cosmetic treatments), multiple sclerosis, spinal cord injury, diabetes, chronic heart disease, end-stage kidney disease, liver failure and in which stem cells are used to replace destroyed or dysfunctional cells. Prevention of such conditions or disorders may be achieved by maintaining stem cells in a protected state by the use of an agent of the invention.

The present invention further provides cells prepared by the methods described hereinabove for the treatment of conditions or disorders typified by a need for stem cells, as described above.

It should be noted that due to the effects of the aforementioned agents on aberrant cell division, even samples of stem cells containing such aberrant cells may be used and a dual effect of reducing the aberrant division while expanding the stem cells may be achieved. Thus the aforementioned agents may be used in vitro, ex vivo or in vivo to protect normal stem/progenitor cells whilst eliminating cells undergoing aberrant cell growth. This is particularly applicable to haematopoietic cells, e.g. when treating leukaemia/lymphoma.

Thus in a particular aspect the present invention provides a method of treating or preventing a condition or disorder in which aberrant cell division occurs. e.g., a cancer, in a human or non-human subject, wherein said method comprises administering an agent of the invention, wherein said agent is capable of both reducing said aberrant cell division and maintaining or expanding stem cells of said subject.

As described above, the agents of the invention, which reduce or prevent PBX-dependent transcription regulation, particularly HOX:PBX antagonists, have various clinical applications and thus a further aspect of the invention provides pharmaceutical compositions containing agents of the invention. The use of these agents as a medicament forms a further aspect of the invention.

Thus, in a further aspect the present invention provides a pharmaceutical composition comprising an agent of the invention, which reduces or prevents PBX-dependent transcription regulation as described hereinabove, suitably an antagonist, suitably an antagonist of the interaction between HOX and PBX, or a polynucleotide or vector capable of expressing such a peptide, and a pharmaceutically acceptable carrier.

Pharmaceutical compositions as described herein for use as a medicament, in particular for use in treating or preventing disorders or conditions typified by aberrant cell division, or disorders or conditions typified by a need for stem cells, such as the conditions described herein, and methods of treatment or prophylaxis using such compositions and use of said agents for the preparation of a medicament for treating or preventing such disorders or conditions, form further aspects of the invention.

"Pharmaceutically acceptable" as referred to herein refers to ingredients that are compatible with other ingredients of the compositions as well as physiologically acceptable to the recipient.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

Pharmaceutical compositions according to the invention may be formulated in conventional manner using readily available ingredients. Thus, the active ingredient (i.e. the peptide) may be incorporated, optionally together with other active substances, with one or more conventional carriers, diluents and/or excipients, to produce conventional galenic preparations such as tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, sterile packaged powders, and the like.

The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, polylactone, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of an agent of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Dosages of agents of the invention employed in practising the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The present invention further provides anhydrous pharmaceutical compositions and dosage forms comprising the agents of the invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The agent of the invention may be administered either simultaneously with, or before or after, one or more other therapeutic agent. The agent of the invention may be administered separately, by the same or different route of administration, or together in the same pharmaceutical composition as the other agents.

In one embodiment, the invention provides a product comprising an agent of the invention and at least one other therapeutic agent as a combined preparation for simultaneous, separate or sequential use in therapy. In one embodiment, the therapy is the treatment of a condition or disorder in which aberrant cell division occurs. Products provided as a combined preparation include a composition comprising the agent of the invention and the other therapeutic agent(s) together in the same pharmaceutical composition, or the agent of the invention and the other therapeutic agent(s) in separate form, e.g. in the form of a kit.

In one embodiment, the invention provides a pharmaceutical composition comprising an agent of the invention and another therapeutic agent(s). Optionally, the pharmaceutical composition may comprise a pharmaceutically acceptable excipient, as described above.

A skilled person will appreciate that an agent of the invention may be administered to a subject, particularly a human subject, wherein the subject is being treated with surgery or radiotherapy for a condition or disorder in which aberrant cell division occurs. A compound of the invention may also be administered to a subject, particularly a human subject, wherein the subject has previously (e.g. within 24 hours) been treated with surgery or radiotherapy for a condition or disorder in which aberrant cell division occurs. A subject, particularly a human subject may also be treated with surgery or radiotherapy for a condition or disorder in which aberrant cell division occurs wherein a compound of the invention has previously (e.g. within 24 hours) been administered to a subject, In one embodiment, the invention provides a kit comprising two or more separate pharmaceutical compositions, at least one of which contains an agent of the invention. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the agent of the invention and the other therapeutic agent may be manufactured and/or formulated by the same or different manufacturers. Moreover, the agent of the invention and the other therapeutic may be brought together into a combination therapy: (i) prior to release of the combination product to physicians (e.g. in the case of a kit comprising the agent of the invention and the other therapeutic agent); (ii) by the physician themselves (or under the guidance of the physician) shortly before administration; (iii) in the patient themselves, e.g. during sequential administration of the agent of the invention and the other therapeutic agent.

Accordingly, the invention provides the use of an agent of the invention for treating a condition or disorder in which aberrant cell division occurs, wherein the medicament is prepared for administration with another therapeutic agent. The invention also provides the use of another therapeutic agent for treating a condition or disorder in which aberrant cell division occurs, wherein the medicament is administered with an agent of the invention.

The invention also provides an agent of the invention for use in a method of treating a condition or disorder in which aberrant cell division occurs, wherein the agent of the invention is prepared for administration with another therapeutic agent. The invention also provides another therapeutic agent for use in a method of treating a condition or disorder in which aberrant cell division occurs, wherein the other therapeutic agent is prepared for administration with an agent of the invention. The invention also provides an agent of the invention for use in a method of treating a condition or disorder in which aberrant cell division occurs, wherein agent of the invention is administered with another therapeutic agent. The invention also provides another therapeutic agent for use in a method of treating a condition or disorder in which aberrant cell division occurs, wherein the other therapeutic agent is administered with an agent of the invention.

The invention also provides the use of an agent of the invention for treating a condition or disorder in which aberrant cell division occurs, wherein the subject has previously (e.g. within 24 hours) been treated with another therapeutic agent. The invention also provides the use of another therapeutic agent for treating a condition or disorder in which aberrant cell division occurs, wherein the subject has previously (e.g. within 24 hours) been treated with an agent of the invention.

Compositions may additionally comprise molecules which assist or augment the action of the agents of the invention, e.g. cytotoxic agents such as antimetabolites, alkylating agents, cytotoxic antibiotics, topoisomerase I and/or II inhibitors, vinca alkaloids and monoclonal antibodies.

If required, the compositions may also contain targeting moieties attached to the active ingredient, e.g. a ligand which binds specifically and selectively to an endogenous receptor to allow targeting to a particular cell type or location, such as targeting to lymphocytes, monocytes, macrophages, endothelial cells, epithelial cells, blood cells, erythrocytes, platelets, eosinophils, neutrophils, natural killer cells, dendritic cells, brain cells, heart cells, lung cells, islet cells, kidney cells, cancer cells, hormonal gland cells, skin, bone, joints, bone marrow, gastric mucosa, lymph nodes, peyers patches, the omentum and other appropriate tissues.

Peptides of the invention may be used to assist or augment the action of agents used for conventional treatments, e.g. cytotoxic agents, to reduce their side effects, e.g. by protection of stem cells during treatment.

In one embodiment, a peptide of the invention is administered alongside one or more other therapeutically active agents. For example, a peptide of the invention may be used as a combinatorial chemotherapeutic agent. Peptides of the invention may induce some cancer cells, e.g. AML cells, to enter the cell cycle. Cells which have been stimulated in this way may therefore become more susceptible to conventional anti-cancer drugs. The peptides of the invention may therefore be used in combination with other anti-cancer agents, such as cytotoxic drugs, to target cancers such as leukaemia, for example AML.

Peptides of the invention may also be used in combination with other anticancer therapies in order to protect the endogenous stem cell population. The peptides of the invention may maintain normal stem/progenitor cells in a G0/G1 quiescent state. This cytoprotective ability may thus protect such stem cells from the effects of any anti-cancer treatment. This may be of particular use where the peptides of the invention are used in combination with cytotoxic agents which target dividing cells. By maintaining the normal stem cells of the patient in a quiescent state during such treatment, the side effects of the anti-cancer treatment on the endogenous stem cell population can be minimised.

This reduction in the potential side effects may also allow a higher dose or level of the conventional treatment to be used on the patient than would otherwise be possible or safe.

In one embodiment, the other therapeutic agent is an anti-tumour agent selected from the group consisting of antiproliferative agents, kinase inhibitors, angiogenesis inhibitors, growth factor inhibitors, cox-I inhibitors, cox-II inhibitors, mitotic inhibitors, alkylating agents, antimetabolites, intercalating antibiotics, growth factor inhibitors, radiation, cell cycle inhibitors, enzymes, topoisomerase inhibitors, biological response modifiers, antibodies, cytotoxics, anti-hormones, statins, anti-androgens and photochemotherapy agents.

Accordingly, the invention includes as a further aspect a combination of an agent of the invention with an anti-tumour agent selected from the group consisting of antiproliferative agents, kinase inhibitors, angiogenesis inhibitors, growth factor inhibitors, cox-I inhibitors, cox-II inhibitors, mitotic inhibitors, alkylating agents, antimetabolites, intercalating antibiotics, growth factor inhibitors, radiation, cell cycle inhibitors, enzymes, topoisomerase inhibitors, biological response modifiers, antibodies, cytotoxics, anti-hormones, statins, anti-androgens and photochemotherapy agents.

In one embodiment of the present invention the anti-tumor agent used in conjunction with a composition of the present invention is an anti-angiogenesis agent, kinase inhibitor, pan kinase inhibitor or growth factor inhibitor.

Suitable pan kinase inhibitors include SU-11248 (sutinib malate), described in U.S. Pat. No. 6,573,293 (Pfizer Inc).

Anti-angiogenesis agents, include but are not limited to the following agents, such as EGF inhibitors, EGFR inhibitors, VEGF inhibitors, VEGFR inhibitors, TIE2 inhibitors, IGF1 R inhibitors, COX-II (cyclooxygenase II) inhibitors, MMP-2 (matrix-metalloprotienase 2) inhibitors, and MMP-9 (matrix-metalloprotienase 9) inhibitors. Suitable VEGF inhibitors, include for example, Avastin (bevacizumab), an anti-VEGF monoclonal antibody of Genentech, Inc. of South San Francisco, Calif.

Additional VEGF inhibitors include CP-547,632 (Pfizer Inc.), AG13736 (axitinib, Pfizer Inc.), ZD-6474 (AstraZeneca), AEE788 (Novartis), AZD-2171), VEGF Trap (Regeneron/Aventis), Vatalanib (also known as PTK-787, ZK-222584: Novartis & Schering AG), Macugen (pegaptanib octasodium, NX-1838, EYE-001, Pfizer Inc./Gilead/Eyetech), IM862 (Cytran Inc. of Kirkland, Wash., USA); and Angiozyme, a synthetic ribozyme from Ribozyme (Boulder, Colo.) and Chiron (Emeryville, Calif.) and combinations thereof. VEGF inhibitors useful in the practice of the present invention are disclosed in U.S. Pat. Nos. 6,534,524 and 6,235,764, both of which are incorporated in their entirety for all purposes. Particularly suitable VEGF inhibitors include CP-547,632, axitinib, Vatalanib, Macugen and combinations thereof.

Other antiproliferative agents that may be used with the compositions of the present invention include inhibitors of the enzyme farnesyl protein transferase and inhibitors of the receptor tyrosine kinase PDGFr. PDGRr inhibitors include but are not limited to those disclosed in international patent application publication number WO01/40217, published Jul. 7, 2001 and international patent application publication number WO2004/020431, published Mar. 11, 2004, the contents of which are incorporated in their entirety for all purposes. Suitable PDGFr inhibitors include Pfizer's CP-673,451 and CP-868,596 and its pharmaceutically acceptable salts.

Suitable GARF inhibitors include Pfizer's AG-2037 (pelitrexol and its pharmaceutically acceptable salts). GARF inhibitors useful in the practice of the present invention are disclosed in U.S. Pat. No. 5,608,082 which is incorporated in its entirety for all purposes.

Examples of useful COX-11 inhibitors which can be used in conjunction with compounds of the invention described herein include CELEBREX (celecoxib), parecoxib, deracoxib, ABT-963, MK-663 (etoricoxib), COX-189 (Lumiracoxib), BMS 347070, RS 57067, NS-398, Bextra (valdecoxib), paracoxib, Vioxx (rofecoxib), SD-8381, 4-Methyl-2-(3,4-dimethylphenyl)-1-(4-sulfamoyl-phenyl)-1H-pyrrole, 2-(4-Ethoxyphenyl)-4-methyl-1-(4-sulfamoylphenyl)-1H-pyrrole, T-614, JTE-522, S-2474, SVT-2016, CT-3, SC-58125 and Arcoxia (etoricoxib). Additionally, COX-11 inhibitors are disclosed in U.S. patent application Ser. Nos. 10/801,446 and 10/801,429, the contents of which are incorporated in their entirety for all purposes Other useful inhibitors as anti-tumor agents used in conjunction with compositions of the present invention include aspirin, and non-steroidal anti-inflammatory drugs (NSAIDs) which inhibit the enzyme that makes prostaglandins (cyclooxygenase I and II), resulting in lower levels of prostaglandins, include but are not limited to the following, Salsalate (Amigesic), Diflunisal (Dolobid), Ibuprofen (Motrin), Ketoprofen (Orudis), Nabumetone (Relafen), Piroxicam (Feldene), Naproxen (Aleve, Naprosyn), Diclofenac (Voltaren), Indomethacin (Indocin), Sulindac (Clinoril), Tolmetin (Tolectin), Etodolac (Lodine), Ketorolac (Toradol), Oxaprozin (Daypro) and combinations thereof.

Suitable COX-I inhibitors include ibuprofen (Motrin), nuprin, naproxen (Aleve), indomethacin (Indocin), nabumetone (Relafen) and combinations thereof.

Targeted agents used in conjunction with a composition of the present invention include EGFr inhibitors such as Iressa (gefitinib, AstraZeneca), Tarceva (erlotinib or OSI-774, OSI Pharmaceuticals Inc.), Erbitux (cetuximab, Imclone Pharmaceuticals, Inc.), EMD-7200 (Merck AG), ABX-EGF (Amgen Inc. and Abgenix Inc.), HR3 (Cuban Government), IgA antibodies (University of Erlangen-Nuremberg), TP-38 (IVAX), EGFR fusion protein, EGF-vaccine, anti-EGFr immunoliposomes (Hermes Biosciences Inc.) and combinations thereof. Suitably EGFr inhibitors include Iressa, Erbitux, Tarceva and combinations thereof. Other anti-tumor agents include those selected from pan erb receptor inhibitors or ErbB2 receptor inhibitors, such as CP-724,714 (Pfizer, Inc.), CM 033 (canertinib, Pfizer, Inc.), Herceptin (trastuzumab, Genentech Inc.), Omitarg (2C4, pertuzumab, Genentech Inc.), TAK-165 (Takeda), GW-572016 (lonafamib, GlaxoSmithKline), GW-282974 (GlaxoSmithKline), EKB-569 (Wyeth), PKM 66 (Novartis), dHER2 (HER2 Vaccine, Corixa and GlaxoSmithKline), APC8024 (HER2 Vaccine, Dendreon), anti-HER2/neu bispecific antibody (Decof Cancer Center), B7.her2.IgG3 (Agensys), AS HER2 (Research Institute for Rad Biology & Medicine), trifuntional bispecific antibodies (University of Munich) and mAB AR-209 (Aronex Pharmaceuticals Inc) and mAB 2B-1 (Chiron) and combinations thereof. Particular erb selective anti-tumor agents include Herceptin, TAK-165, CP-724, 714, ABX-EGF, HER3 and combinations thereof. Suitably pan erb receptor inhibitors include GW572016, CM 033, EKB-569, and Omitarg and combinations thereof.

Additionally, other anti-tumor agents may be selected from the following agents, BAY-43-9006 (Onyx Pharmaceuticals Inc.), Genasense (augmerosen, Genta), Panitumumab (Abgenix/Amgen), Zevalin (Schering), Bexxar (Corixa/GlaxoSmithKline), Abarelix, Alimta, EPO 906 (Novartis), discodermolide (XAA-296), ABT-510 (Abbott), Neovastat (Aeterna), enzastaurin (Eli Lilly), Combrestatin A4P (Oxigene), ZD-6126 (AstraZeneca), flavopiridol (Aventis), CYC-202 (Cyclacel), AVE-8062 (Aventis), DMXAA (Roche/Antlsoma), Thymitaq (Eximias), Temodar (temozolomide, Schering Plough) and Revilimd (Celegene) and combinations thereof.

Other anti-tumor agents may be selected from the following agents, CyPat (cyproterone acetate), Histerelin (histrelin acetate), Plenaixis (abarelix depot), Atrasentan (ABT-627), Satraplatin (JM-216), thalomid (Thalidomide), Theratope, Temilifene (DPPE)1 ABI-007 (paclitaxel), Evista (raloxifene), Atamestane (Biomed-777), Xyotax (polyglutamate paclitaxel), Targetin (bexarotine) and combinations thereof.

Additionally, other anti-tumor agents may also be selected from the following agents, Trizaone (tirapazamine), Aposyn (exisulind), Nevastat (AE-941), Ceplene (histamine dihydrochloride), Orathecin (rubitecan), Virulizin, Gastrimmune (G17DT), DX-8951f (exatecan mesylate), Onconase (ranpimase), BEC2 (mitumoab), Xcytrin (motexafin gadolinium) and combinations thereof. Further anti-tumor agents may selected from the following agents, CeaVac (CEA), NeuTrexin (trimetresate glucuronate) and combinations thereof. Additional anti-tumor agents may selected from the following agents, OvaRex (oregovomab), Osidem (IDM-1), and combinations thereof.

Additional anti-tumor agents may selected from the following agents, Advexin (ING 201), Tirazone (tirapazamine), and combinations thereof. Additional anti-tumor agents may selected from the following agents, RSR13 (efaproxiral), Cotara (1311 chTNT 1/b), NBI-3001 (IL-4) and combinations thereof. Additional anti-tumor agents may selected from the following agents, Canvaxin, GMK vaccine, PEG Interon A, Taxoprexin (DHA/paclitaxel) and combinations thereof.

Other anti-tumor agents include Pfizer's MEK1/2 inhibitor PD325901, Array Biopharm's MEK inhibitor ARRY-142886, Bristol Myers' CDK2 inhibitor BMS-387,032, Pfizer's CDK inhibitor PD0332991 and AstraZeneca's AXD-5438 and combinations thereof.

Additionally, mTOR inhibitors may also be utilized such as CCI-779 (Wyeth) and rapamycin derivatives RAD001 (Novartis) and AP-23573 (Ariad), HDAC inhibitors SAHA (Merck Inc/Aton Pharmaceuticals) and combinations thereof. Additional anti-tumor agents include aurora 2 inhibitor VX-680 (Vertex), Chk1/2 inhibitor XL844 (Exilixis).

The following cytotoxic agents, e.g., one or more selected from the group consisting of epirubicin (Ellence), docetaxel (Taxotere), paclitaxel, Zinecard (dexrazoxane), rituximab (Rituxan), imatinib mesylate (Glivec), and combinations thereof, may be used in conjunction with a composition of the present invention as described herein.

The invention also contemplates the use of the compositions of the present invention together with hormonal therapy, including but not limited to, exemestane (Aromasin, Pfizer Inc.), leuprorelin (Lupron or Leuplin, TAP/Abbott/Takeda), anastrozole (Arimidex, Astrazeneca), gosrelin (Zoladex, AstraZeneca), doxercalciferol, fadrozole, formestane, tamoxifen citrate (tamoxifen, Nolvadex, AstraZeneca), Casodex (AstraZeneca), Abarelix (Praecis), Trelstar, and combinations thereof.

The invention also relates to hormonal therapy agents such as anti-estrogens including, but not limited to fulvestrant, toremifene, raloxifene, lasofoxifene, letrozole (Femara, Novartis), anti-androgens such as bicalutamide, flutamide, mifepristone, nilutamide, Casodex® (4'-cyano-3-(4-fluorophenylsulphonyl)-2-hydroxy-2-methyl-3'-(trifluoromethyl) propionanilide, bicalutamide) and combinations thereof.

Further, the invention provides a composition of the present invention alone or in combination with one or more supportive care products, e.g., a product selected from the group consisting of Filgrastim (Neupogen), ondansetron (Zofran), Fragmin, Procrit, Aloxi, Emend, or combinations thereof.

Particularly suitable cytotoxic agents include Camptosar, Erbitux, Iressa, Glivec, Taxotere and combinations thereof.

The following topoisomerase I inhibitors may be utilized as anti-tumor agents: camptothecin; irinotecan HCl (Camptosar); edotecarin; orathecin (Supergen); exatecan (Daiichi); BN-80915 (Roche); and combinations thereof. Particularly preferred toposimerase II inhibitors include epirubicin (Ellence).

Alkylating agents include, but are not limited to, nitrogen mustard N-oxide, cyclophosphamide, ifosfamide, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, ifosfamide, KW-2170, mafosfamide, and mitolactol; platinum-coordinated alkylating compounds include but are not limited to, cisplatin, Paraplatin (carboplatin), eptaplatin, lobaplatin, nedaplatin, Eloxatin (oxaliplatin, Sanofi) or satrplatin and combinations thereof. Particularly preferred alkylating agents include Eloxatin (oxaliplatin).

Antimetabolites include but are not limited to, methotrexate, 6-mercaptopurine riboside, mercaptopurine, 5-fluorouracil (5-FU) alone or in combination with leucovorin, tegafur, LIFT, doxifluridine, carmofur, cytarabine, cytarabine ocfosfate, enocitabine, S-1, Alimta (premetrexed disodium, LY231514, MTA), Gemzar (gemcitabine, Eli Lilly), fludarabin, 5-azacitidine, capecitabine, cladribine, clofarabine, decitabine, eflornithine, ethynylcytidine, cytosine arabinoside, hydroxyurea, TS-1, melphalan, nelarabine, nolatrexed, ocfosfate, disodium premetrexed, pentostatin, pelitrexoi, raltitrexed, triapine, trimetrexate, vidarabine, vincristine, vinorelbine; for example, one of the preferred antimetaboiites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid and combinations thereof.

Antibiotics include intercalating antibiotics but are not limited to: aclarubicin, actinomycin D, amrubicin, annamycin, adriamycin, bleomycin, daunorubicin, doxorubicin, elsamitrucin, epirubicin, galarubicin, idarubicin, mitomycin C, nemorubicin, neocarzinostatin, peplomycin, pirarubicin, rebeccamycin, stimalamer, streptozocin, valrubicin, zinostatin and combinations thereof.

Plant derived anti-tumor substances include for example those selected from mitotic inhibitors, for example vinblastine, docetaxel (Taxotere), paclitaxel and combinations thereof.

Cytotoxic topoisomerase inhibiting agents include one or more agents selected from the group consisting of aclarubicn, amonafide, belotecan, camptothecin, 10-hydroxycamptothecin, 9-aminocamptothecin, diflomotecan, irinotecan HCl (Camptosar), edotecarin, epirubicin (Eilence), etoposide, exatecan, gimatecan, lurtotecan, mitoxantrone, pirarubicin, pixantrone, rubitecan, sobuzoxane, SN-38, tafluposide, topotecan, and combinations thereof. Preferred cytotoxic topoisomerase inhibiting agents include one or more agents selected from the group consisting of camptothecin, 10-hydroxycamptothecin, 9-aminocamptothedn, irinotecan HCl (Camptosar), edotecarin, epirubicin (Eilence), etoposide, SN-38, topotecan, and combinations thereof.

Immunologicals include interferons and numerous other immune enhancing agents. Interferons include interferon alpha, interferon alpha-2a, interferon, alpha-2b, interferon beta, interferon gamma-1a, interferon gamma-1b (Actimmune), or interferon gamma-n1 and combinations thereof. Other agents include filgrastim, ientinan, sizofilan, TheraCys, ubenimex, WF-10, aldesleukin, alemtuzumab, BAM-002, dacarbazine, daclizumab, denileukin, gemtuzumab ozogamicin, ibritumomab, imiquimod, lenograstim, lentinan, melanoma vaccine (Corixa), molgramostim, OncoV AX-CL, sargramostim, tasonermin, tecleukin, thymalasin, tositumomab, Virulizin, 2-100, epratuzumab, mitumomab, oregovomab, pemtumomab (Y-muHMFGI), Provenge (Dendreon) and combinations thereof.

Biological response modifiers are agents that modify defense mechanisms of living organisms or biological responses, such as survival, growth, or differentiation of tissue cells to direct them to have anti-tumor activity. Such agents include krestin, lentinan, sizofiran, picibanil, ubenimex and combinations thereof.

Other anticancer agents include alitretinoin, ampligen, atrasentan bexarotene, bortezomib. Bosentan, calcitriol, exisuiind, finasteride.fotemustine, ibandronic acid, miltefosine, mitoxantrone, 1-asparaginase, procarbazine, dacarbazine, hydroxycarbamide, pegaspargase, pentostatin, tazarotne, Telcyta (TLK-286, Telik Inc.), Velcade (bortemazib, Millenium), tretinoin, and combinations thereof.

Other anti-angiogenic compounds include acitretin, fenretinide, thalidomide, zoledronic acid, angiostatin, aplidine, cilengtide, combretastatin A-4, endostatin, halofuginone, rebimastat, removab, Revlimid, squalamine, ukrain, Vitaxin and combinations thereof. Platinum-coordinated compounds include but are not limited to, cisplatin, carboplatin, nedaplatin, oxaliplatin, and combinations thereof.

Camptothecin derivatives include but are not limited to, camptothecin, 10-hydroxycamptothecin, 9-aminocamptothecin, irinotecan, SN-38, edotecarin, topotecan and combinations thereof. Other antitumor agents include mitoxantrone, 1-asparaginase, procarbazine, dacarbazine, hydroxycarbamide, pentostatin, tretinoin and combinations thereof.

Anti-tumor agents capable of enhancing antitumor immune responses, such as CTLA4 (cytotoxic lymphocyte antigen 4) antibodies, and other agents capable of blocking CTLA4 may also be utilized, such as MDX-010 (Medarex) and CTLA4 compounds disclosed in U.S. Pat. No. 6,682, 736; and anti-proliferative agents such as other farnesyl protein transferase inhibitors, for example the farnesyl protein transferase inhibitors. Additionally, specific CTLA4 antibodies that can be used in the present invention include those described in U.S. Provisional Application No. 60/113, 647 (filed Dec. 23, 1998), U.S. Pat. No. 6,682,736 both of which are herein incorporated by reference in their entirety.

Specific IGF1R antibodies that can be used in the present invention include those. described in International Patent Application No. WO 2002/053596, which is herein incorporated by reference in its entirety. Specific CD40 antibodies that can be used in the present invention include those described in International Patent Application No. WO 2003/040170 which is herein incorporated by reference in its entirety.

Gene therapy agents may also be employed as anti-tumor agents such as TNFerade (GeneVec), which express TNFalpha in response to radiotherapy.

In one embodiment of the present invention statins may be used in conjunction with a composition of the present invention. Statins (HMG-CoA reducatase inhibitors) may be selected from the group consisting of Atorvastatin (Lipitor, Pfizer Inc.), Pravastatin (Pravachol, Bristol-Myers Squibb), Lovastatin (Mevacor, Merck Inc.), Simvastatin (Zocor, Merck Inc.), Fluvastatin (Lescol, Novartis), Cerivastatin (Baycol, Bayer), Rosuvastatin (Crestor, AstraZeneca), Lovastatin and Niacin (Advicor, Kos Pharmaceuticals), derivatives and combinations thereof. In a preferred embodiment the statin is selected from the group consisting of Atovorstatin and Lovastatin, derivatives and combinations thereof. Other agents useful as anti-tumor agents include Caduet.

In one embodiment of the invention, the compositions of the present invention may be used in conjunction with photochemotherapy agents which are used to generate reactive oxygen species locally. Examples of photochemotherapy agents include palladium bacteriophephorbide (TOOKAD) used in photodynamic therapy; psoralen, 8-methoxypsoralen/methoxsalen (Oxsoralen-Ultra®, 8-MOP®, Oxsoralen®, Uvadex®), 4,5,8-trimethylpsoralen/trioxsalen (Trisoralen®), used in PUVA (Psoralen Ultra Violet A light); UVAR or UVAR® XTS™ Photopheresis System (Therakos, Inc., Exton, Pa.): Theraflex ECP® (Macopharma); CobeSpectra+Photo Immune System UVA PIT (Med Tech Solution); photosensitizers such as calcipotriene, tazarotene, chrysarobin and its synthetic derivative anthralin/1,8-dihydroxy-9-anthrone/dithranol (Drithocreme®); firefly (*Photinus pyralis*) luciferase used in (BioLuminescence Activated Destruction (BLADe)); erythrosin B (EB); erythrosine sodium; m-tetra(hydroxyphenyl)chlorin (m-THPC)/temoporfin (Foscan®, Biolitec AG); porphyrins such as d-aminolevulinic acid (d-ALA) (Levulan Kerastick®; DUSA Pharmaceuticals, Inc.), 5-ALA methylester (MLA/M-ALA) (Metvix®; PhotoCure ASA), 5-ALA benzylesther (Benzvix®); 5-ALA hexylesther (Hexvix®), tin ethyl etiopurpurin (SnET2)/Sn etiopurpurin/rostaporfin (Photrex®, Purlytin®; Miravant MedicalTechnologies, boronated protoporphyrin (BOPP®), 2-(1-hexyloxyethyl)-2-divinyl pyropheophorbide-a (HPPH) (Photochlor®; Rosewell Park Cancer Institute), texaphyrins including europium texaphyrin (Eu-Tex), dysprosium texaphyrin (Dy-Tex), manganese texaphyrin (Mn-Tex), lutetium texaphyrin/PCI-0123 (Lu-Tex®, Lutex®, Lutrin®), motexafin lutetium (MLu)/lutetium(III) texaphyrin (Lu-Tex) (Antrin®, Lutrin®, Optrin®; Pharmacyclics Inc.), motexafin gadolinium (MGd)/PCI-0120 (Xcytrin®; source: Pharmacyclics Inc.) phthalocyanine-4 (Pc 4), taporfin sodium/NPe6/mono-L-aspartyl chlorin e6/taporfin sodium/LS11 (Talaporfin®; Light ScienceCorporation), benzoporphyrin derivative-monoacid ring A (BPD-MA)/verteporfin (Visudyne®, Novartis Pharmaceuticals), hematoporphyrin derivative (HpD) partially purified, porfimer sodium (Photofrin®; Axcan Pharma, Inc.), dihematoporphyrin ethers (DHE), photosan-3 (PS-3), photofrin-II, meso-tetrakis-phenylporphyrin (TPP) and tetraphenylporphinesulfonate (TPPS4)

The following Examples illustrate the invention:

EXAMPLE 1: EFFECT OF PEPTIDES ON CELL VIABILITY IN VITRO

In this example peptides of the invention were used in in vitro assays to determine their effects on cell death and cell proliferation in a variety of cell lines.

Methods

1. Peptide Design

The following peptides were constructed:

HXR9 (SEQ ID NO.86) is known to prevent the interaction between PBX and HOX proteins to inhibit the growth of a number of different cancers both in vitro and in mouse models (Morgan, R., Pirard, P. M., Shears, L., Sohal, J., Pettengell, R. & Pandha, H. S. (2007) Antagonism of HOX/PBX dimer formation blocks the in vivo proliferation of melanoma. *Cancer Res*, 67, 5806-5813; Shears, L., Plowright, L., Harrington, K., Pandha, H. S. & Morgan, R. (2008) Disrupting the interaction between HOX and PBX causes necrotic and apoptotic cell death in the renal cancer lines CaKi-2 and 769-P. *J Urol*, 180, 2196-2201; Plowright, L., Harrington, K. J., Pandha, H. S. & Morgan, R. (2009) HOX transcription factors are potential therapeutic targets in non-small-cell lung cancer (targeting HOX genes in lung cancer). *Br J Cancer*, 100, 470-475; Daniels, T. R., Neacato, II, Rodriguez, J. A., Pandha, H. S., Morgan, R. & Penichet, M.

L. (2010) Disruption of HOX activity leads to cell death that can be enhanced by the interference of iron uptake in malignant B cells. *Leukemia*, 24, 1555-1565; Morgan, R., Plowright, L., Harrington, K. J., Michael, A. & Pandha, H. S. (2010) Targeting HOX and PBX transcription factors in ovarian cancer. *BMC Cancer*, 10, 89; Morgan, R., Boxall, A., Harrington, K. J., Simpson, G. R., Gillett, C., Michael, A. & Pandha, H. S. (2012) Targeting the HOX/PBX dimer in breast cancer. *Breast Cancer Res Treat*, 136, 389-398; Errico, M. C., Felicetti, F., Bottero, L., Mattia, G., Boe, A., Felli, N., Petrini, M., Bellenghi, M., Pandha, H. S., Calvaruso, M., Tripodo, C., Colombo, M. P., Morgan, R. & Care, A. (2013) The abrogation of the HOXB7/PBX2 complex induces apoptosis in melanoma through the miR-221&222-c-FOS pathway. *Int J Cancer*, 133, 879-892; Morgan, R., Boxall, A., Harrington, K. J., Simpson, G. R., Michael, A. & Pandha, H. S. (2014) Targeting HOX transcription factors in prostate cancer. *BMC Urol*, 14, 17).

HXR9 (SEQ ID NO: 86) contains the highly conserved HOX hexapeptide sequence WYPWMKK (SEQ ID NO: 85), which is known to mediate this process, linked to a polyarginine peptide previously shown to mediate efficient movement of proteins across cell membranes.

CXR9 (SEQ ID NO: 87) was generated as a control peptide, based on the HXArg9 sequence but with an amino acid substitution in the HOX/PBX interfering peptide sequence and is inactive in the cancer models described above.

HXR9AS7 (SEQ ID NO: 88) is based on the HXArg9 sequence wherein the HOX hexapeptide sequence WYPWMKK (SEQ ID NO: 50) is conserved.

HXR9noH (SEQ ID NO: 89) is based on the HXArg9 sequence wherein the HOX hexapeptide sequence WYPWMKK (SEQ ID NO: 50) is conserved.

HXR9KS3 (SEQ ID NO: 6) based on the HXArg9 sequence but with an amino acid substitution in the HOX/PBX interfering peptide sequence.

HXR9KS3/7 (SEQ ID NO: 7) based on the HXArg9AS7 sequence but with an amino acid substitution in the HOX/PBX interfering peptide sequence.

HXR9KS3noH (SEQ ID NO: 8) based on the HXArg9noH sequence but with an amino acid substitution in the HOX/PBX interfering peptide sequence.

The sequences of these peptides are as follows. All peptides were prepared by routine chemical synthesis. These peptides were synthesised by Sigma-Aldrich at 90% purity and provided as a lyophilized powder. This was dissolved in water to give a stock concentration of 100 mM of each peptide.

```
HXR9 (SEQ ID NO: 86):
WYPWMKKHHRRRRRRRRR

CXR9 (SEQ ID NO: 87):
WYPAMKKHHRRRRRRRRR

HXR9AS7 (SEQ ID NO: 88):
WYPWMKKAARRRRRRRRR

HXR9noH (SEQ ID NO: 89):
WYPWMKKRRRRRRRRR

HXR9KS3 (SEQ ID NO: 6):
WYKWMKKHHRRRRRRRRR

HXR9KS3/7 (SEQ ID NO: 7):
WYKVVMKKAARRRRRRRRR (hereinafter 'HTL001')

HXR9KS3noH (SEQ ID NO: 8):
WYKWMKKRRRRRRRRR
```

2. Assay

The cytotoxicity of the peptides on the prostate cancer derived cell lines DU145 and PC3 was tested as previously described (Morgan et al. 2014, ibid), using the MTT assay for metabolic activity. The cytotoxic drug Docetaxel (a standard chemotherapeutic drug) was included as a positive control. The assay was repeated 3 times and the results are given as the mean IC50 for cell killing±standard deviation.

Results

The dose required to kill 50% of the cells (the IC50) after 2 and 96 hours is shown in the Table 1 below. Doses are in μM (micromoles), and the mean value from 3 experiments is given along with the standard deviation. The fold difference in IC50 relative to HXR9 is also shown in italics.

TABLE 1

Effect of peptides on PC3 cell viability in vitro

| Peptide | PC3 2 hr IC50 (±SD) (change relative to HXR9) | PC3 96 hr IC50 (±SD) (change relative to HXR9) |
| --- | --- | --- |
| CXR9 | >80 | >80 |
| HXR9KS3/7 (HTL001) | 13 (±5) (2.23) | 11 (±4) (3.91) |
| HXR9AS7 | 45 (±19) (0.64) | 40 (±30) (1.08) |
| HXR9KS3 | 19 (±10) (1.53) | 17 (±1) (2.53) |
| HXR9 | 29 (±20) (1) | 43 (±22) (1) |
| HXR9KS3noH | 22 (±6) (1.32) | 21 (±11) (2.05) |
| HXR9noH | 60 (±13) (0.48) | 54 (±18) (0.80) |
| Docetaxel | 4 (±6) | 0 (±0) |

EXAMPLE 2: EFFECT OF PEPTIDES ON CELL VIABILITY IN VITRO

Methods

Peptides

```
HXR9 (SEQ ID NO: 86):
WYPWMKKHHRRRRRRRRR

CXR9 (SEQ ID NO: 87):
WYPAMKKHHRRRRRRRRR

HXR9KS3/7 (SEQ ID NO: 7):
WYKWMKKAARRRRRRRRR (hereinafter 'HTL001')
```

These peptides were synthesised by Sigma-Aldrich at 90% purity and provided as a lyophilized powder. This was dissolved in water to give a stock concentration of 100 mM of each peptide.

Assay

In Vitro Assays for Cell Killing

The cytotoxicity of the peptides on the prostate cancer derived cell lines DU145, LnCaP, and PC3, and the breast cancer derived cell line MDA-MB-231 was tested as previously described (Morgan et al. 2014), using the MTT assay for metabolic activity. 7000-16000 cells, depending on the cell line, were seeded onto 96-well cell plate and treated with 5, 10, 20, 40 and 80 μM of CXR9, HXR9 and HTL001 for 2 h. After treatment, MTT at a final concentration of 0.5 mg/ml was added. Upon 4 h incubation the formed formazan crystals were dissolved in DMSO and the optical density (OD) measured at 540 nm with a spectrofluorimeter. Percentage of cell survival was calculated as a ratio of the mean OD value of treated vs. untreated cells. Experiments were repeated 3 times and statistical analysis performed using Student's t-test. All cell lines were cultured in RPMI media with added 10% FBS, 1% sodium pyruvate and 1% L-Glutamine. They were all cultured in an incubator at 37° C., 5% $CO_2$ The assay was repeated 3 times and the results are given as the mean IC50 for cell killing±standard deviation.
Results As shown in FIG. 1, HTL001 (HXR9KS3/7) is significantly more effective than HXR9 at killing each of the cell types tested:

EXAMPLE 3: LOCALISATION OF HTL001 IN PC3 CELLS

Method

To assess how well HTL001 had bound to PBX proteins throughout the cell, PC3 cells were treated with FAM5-labelled peptide (HTL001/7FAM5), fixed and mounted with Vectashield HardSet Antifade Mounting Medium with Dapi (Vector Laboratories). They were then observed under the Leica Fluorescence microscope.

$1.5 \times 10^5$ of PC3 cells were seeded on 22×22 mm coverslips inside a 6 well plate. After 24-48 h incubation cells were treated with HTL001/7FAM5 for 2 hours. After the incubation period, the media was removed and washed 3 times with PBS. Cooled methanol was added and the coverslips incubated for 10 minutes. The methanol was then removed and left to air dry in the dark for 20 minutes. Coverslips were then washed twice with PBS and mounted on slides using Vectashield HardSet Antifade Mounting Medium with DAPI.
Results HTL001 was taken up by PC3 cells and was found to be present in both the cytoplasm and nucleus, as shown in FIG. 2.

EXAMPLE 4: CFOS EXPRESSION IN PC3 CELLS AFTER HTL001 TREATMENT

Method

PC3 cells were seeded in 25 cm² plates and treated for 2 h with 33 µM CXR9, HXR9 and HTL001 at 80% confluence. RNA was isolated using RNeasy Mini Kit-QIAGEN according to manufacturer's instructions and quantified with NanoDrop ND-1000. cDNA was generated from 1 µg of total RNA using High Capacity cDNA Reverse Transcription Kit in a 25 µl final reaction volume according to the manufacturer protocol. The expression of cFOS was quantified by qRT-PCR. Real-time PCR reactions were performed using 1:10 dilution (5 µl/well) of each cDNA added to TaqMan Universal PCR Master Mix and TaqMan Gene Expression Assay Hs00170630_m1 FOS. Amplification of glyceraldehyde 3-phosphate dehydrogenase (GAPDH) probe was performed as endogenous control. The comparative Ct method (ΔΔCt algorithm) was used for analysis. Independent experiments were performed in triplicates and repeated three times. Statistical analysis was performed with Student's t-test.
Results Both HXR9 and HTL001 treatment caused a significant increase in cFos expression compared to untreated PC3 cells, as shown in FIG. 3. cFos expression was also significantly higher in HTL001 treated cells compared to those treated with HXR9.

These results indicate that cFos can act as a biomarker of tumour response to a peptide of the invention, and as such its elevated expression is a potential surrogate clinical trial endpoint.

EXAMPLE 5: ANNEXIN V-FITC ASSAY

The effect of HTL001 on apoptosis was evaluated using an Annexin V assay. Annexin V binds to phosphatidylserine that translocates from the inner plasma membrane to cell surface soon after initiating apoptosis. Differentiation between apoptosis and necrosis is performed by adding propidium iodide (PI).
Method PC3 cells were seeded in 25 cm² plates and at 80% confluency treated with 33 µM CXR9, HXR9 and HTL001 for 2 h. At the end of the exposure floating and adherent cells were collected by trypsinization, washed in PBS and 4-5× $10^5$ cells were re-suspended in 100 µl of binding buffer. 5 µl of Annexin V-FITC and 0.5 µl of PI were added, mixed and incubated for 15 min in the dark at RT. After incubation, 400 µl of binding buffer was added and the samples were analysed by flow-cytometry. The positive control treated with 2 µM STS for 8 h was separately stained with only Annexin V (channel FL-1), only PI (channel FL-2), and both, for the compensation settings of the two signals. $10^4$ of cells were evaluated in each sample and analysis performed in CellQuest Pro software. Dot-plots (FL-1H/FL-2H) were generated and the cells were divided into live, early apoptotic, late apoptotic and necrotic. Experiments were repeated 3 times and statistical analysis performed using Student's t-test.
Results Both HXR9 and HTL001 treatment caused a significant increase in Annexin staining compared to untreated PC3 cells, as shown in FIG. 4. Annexin staining was significantly higher in HTL001 treated cells compared to those treated with HXR9.

EXAMPLE 6: EFFECT OF HTL001 ON PC3 CELL TUMOUR XENOGRAFTS

Method

PC3 cells were injected subcutaneously into female or male Balb-c nude mice aged 6 to 12 weeks (Harlan, UK). When the tumour size reached 100 mm³ mice were injected intratumouraly with PBS, HXR9 or HTL001 at the intervals shown in FIG. 3. Mice were sacrificed when the tumour size reached 1000 mm³ or at the end of the experiment (36 days). Tumours were then excised and immersed in 10% formalin for 24 h and processed for paraffin embedding. 5 µm slices of xenografts in paraffin blocks were made using microtome and different proteins detected by immunohistochemistry.

Paraffin sections of the PC3 cell line xenografts were de-parafinized and re-hydrated, antigens were retrieved using citrate buffer and endogenous peroxidases quenches using $H_2O_2$. Slides were then blocked with appropriate blocking serum and incubated with primary antibody in blocking serum for 1 h at RT. Primary antibodies to DUSP1 were washed off with PBS and the slides incubated in secondary antibody for 30 min. ABC kit was used according to manufactures instructions to bind peroxidase H to secondary antibody. DAB peroxidase substrate was used for visualisation and nuclei stained with hematoxylin. Sections were counterstained in acid alcohol, blued in Scott's tap water, dehydrated, cleared and mounted with DPX.

Results

HTL001 causes a significant growth retardation of PC3 tumours in mice, as shown in Table 2 and FIGS. 5, 6 and 7.

TABLE 2

Effect of HTL001 on PC3 cell tumour xenografts

| Group | Mean time to RTV2 (days) | Median time to RTV2 (days) | Growth delay (days) | Significance | Maximum % weight loss |
|---|---|---|---|---|---|
| PBS controls | 9.2 | 10.5 | — | — | 0 |
| HXR9 | 17.8 | 18.4 | 7.9 | p > 0.05 ns | 0 |
| HTL001 | 21.0 | 17.2 | 6.7 | p < 0.05 | 0 |

| Group | Mean time to RTV3 (days) | Median time to RTV3 (days) | Growth delay (days) | Significance | Maximum % weight loss |
|---|---|---|---|---|---|
| PBS controls | 12.1 | 13.6 | — | — | 0 |
| HXR9 | 20.8 | 20.8 | 7.2 | p > 0.05 ns | 0 |
| HTL001 | 26.5 | 25.1 | 11.5 | p < 0.01 | 0 |

FIG. 5 shows the mean relative tumour volume treated with HTL001 relative to PBS injected mice as a function of time.

FIG. 6 shows the mean relative % bodyweight of tumour bearing mice treated with HTL001 relative to PBS injected mice as a function of time.

FIG. 7 shows the time to tumor doubling and tripling, relative to PBS injected mice.

EXAMPLE 7: CELL BASED ASSAY FOR HOX/PBX BINDING

Figure 1A:
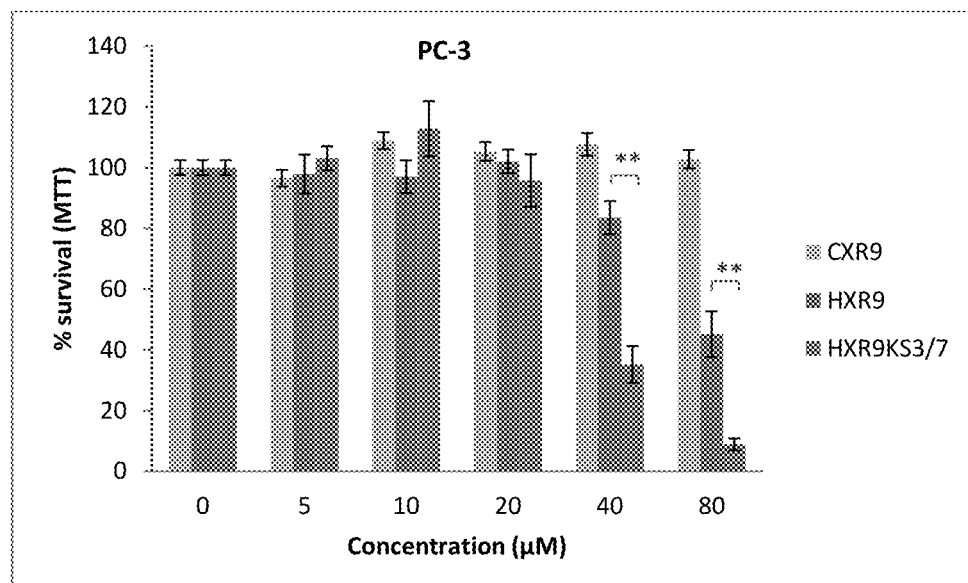
Figure 1B:
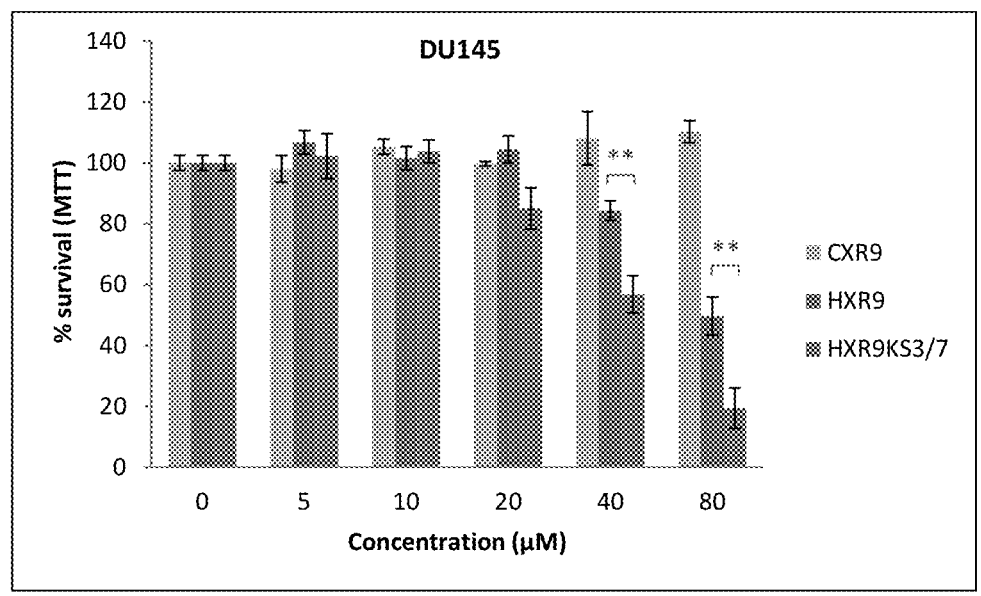
Figure 1C:
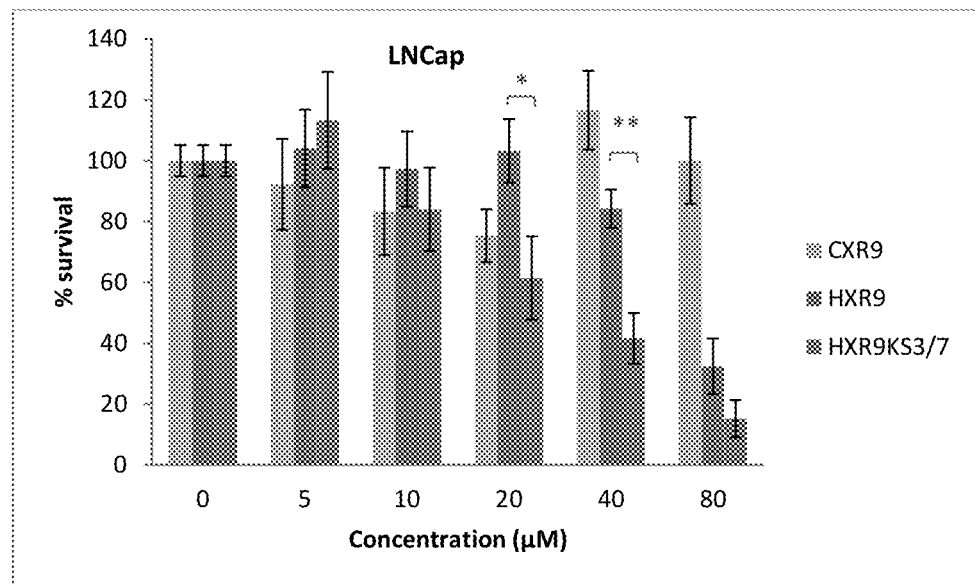
Figure 1D:
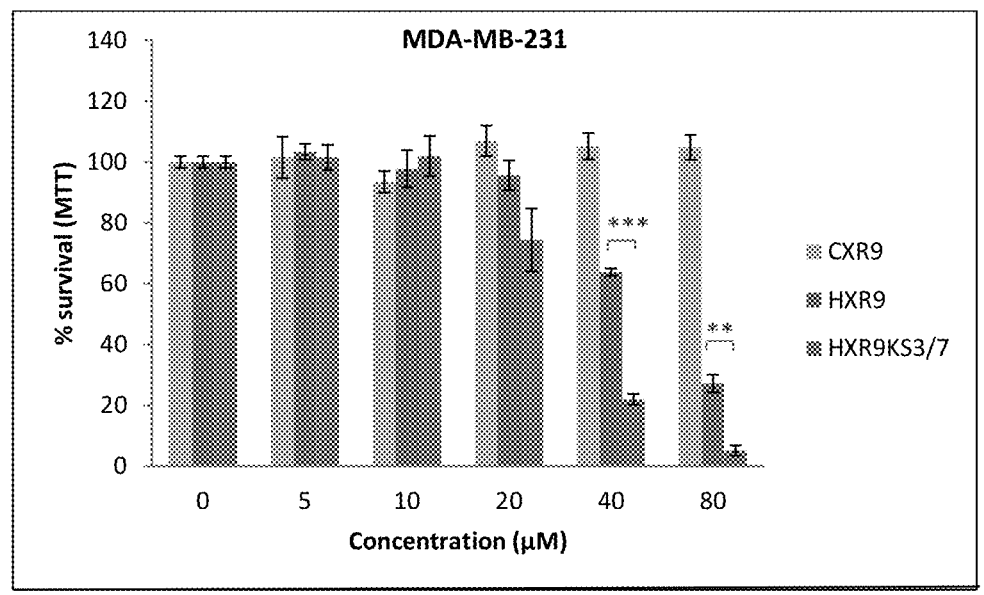

A suitable assay for determining the antagonism activity of a peptide of the invention in relation to the interaction between HOX and PBX is described hereinbelow.

Method

In order to directly assess the ability of each peptide to disrupt HOX/PBX binding a cell-based assay system was developed that could allow the formation of HOX/PBX/DNA dimers. Cultured MDA-MB-231 cells were treated with 10 µM of each peptide for 4 hours and then used to generate a cell lysate using a standard preparation method as described below. HOXB4/PBX2 dimers were then measured using an ELISA-based system as detailed in the table below. The values from this assay are expressed as % inhibition of dimer formation compared to a negative control (DMSO).

Lysate Preparation:

1. Collect approximately 5.0×107 cells by low-speed centrifugation at RT for 5 min. Carefully remove culture medium.

2. Wash the cellular debris (pellet) with PBS at RT, and collect by low-speed centrifugation. Carefully remove supernatant (total protein).

3. Add 1.0 ml of pre-cold RIPA buffer (or other appropriate buffer) with freshly added (Protease Inhibitors) and/or (Phosphatase Inhibitors). Gently resuspend cells in RIPA buffer with a pipet and incubate on ice for 30 min.

4. Further disrupt and homogenize cells by passing through a 21-gauge needle, dounce homogenization or sonication, taking care not to raise the temperature of the lysate. (Optional: Add 10 µl of 10 mg/ml PMSF stock) Incubate 30 min on ice.

5. Transfer to microcentrifuge tube(s) and centrifuge at 10,000×g for 10 min at 4° C. The supernatant fluid is the total cell lysate. Transfer the supernatant to a new microfuge tube and discard the pellet.

Assay Method:

All volumes 0.1 ml unless specified; RT. Plates washed by submersion.

| Step | Process | Time (mins) | Resource |
|---|---|---|---|
| 1 | Coat plates | 60 | 0.2 mg/ml streptavidin (Sigma 85878 1 mg, dissolve in 5 ml PBST) |
| 2 | Wash | ×4 | PBST |
| 3 | Anti-mouse Ab biotin | 30 | Donkey anti-mouse-biotin, ab7060, use at 1:1000 |
| 4 | Wash | ×4 | PBST |
| 5 | Anti-PBX2 | 30 | mAb to PBX2, ab55498, use at 1:500 |
| 6 | Wash | ×4 | PBST |
| 7 | Block | 60 | T20 |
| 8 | Wash | ×4 | PBST |
| 7 | Cell lysate | 30 | Diluted to 100 µg/ml in PBST |
| 8 | Wash | ×4 | PBST |
| 9 | Anti-HOXB4 | 30 | Rabbit anti-HOXB4, ab56049, use at 1:10,000 |
| 10 | Wash | ×4 | PBST |
| 11 | Anti-rabbit AP | 30 | Goat anti-rabbit AP, ab6722, use at 1:3000 |
| 12 | Wash | ×4 | PBST |
| 13 | Wash | ×1 | TBS |
| 14 | Colour development | 30 | pNpp solution |

A schematic diagram for HOXB4/PBX2 dimer assay is shown in FIG. 8.

Results

HTL001 showed a 28.2 (SEM 4.4) % inhibition of HOXB4/PBX2 dimer formation.

EXAMPLE 8: EXPRESSION OF DUSP1 PROTEIN IN HTL001 (HXR9KS3/7) TREATED PC3 CELL LINE TUMOUR XENOGRAFTS

The expression of DUSP1 protein, previously identified as a target of HXR9 (Morgan et al. 2007, ibid), was examined in PC3 tumours removed from mice after intra-tumoural treatment with PBS alone, HXR9 or HTL001. As shown in FIG. 9, DUSP1 expression (brown staining) is considerably increased after HTL001 treatment.

These results indicate that DUSP1 protein can act as a biomarker of tumour response to a peptide of the invention, and as such its elevated expression is a potential surrogate clinical trial endpoint.

SEQUENCE LISTING

<160> NUMBER OF SEQ ID NOS: 93

<210> SEQ ID NO 1

```
<211> LENGTH: 11
<212> TYPE: PRT
<213> ORGANISM: Artificial sequence
<220> FEATURE:
<223> OTHER INFORMATION: Synthetic peptide

<400> SEQUENCE: 1

Arg Arg Arg Arg Arg Arg Arg Arg Arg Arg Arg
1               5                   10

<210> SEQ ID NO 2
<211> LENGTH: 12
<212> TYPE: PRT
<213> ORGANISM: Artificial sequence
<220> FEATURE:
<223> OTHER INFORMATION: Synthetic peptide

<400> SEQUENCE: 2

Arg Arg Arg Arg Arg Arg Arg Arg Arg Arg Arg Arg
1               5                   10

<210> SEQ ID NO 3
<211> LENGTH: 9
<212> TYPE: PRT
<213> ORGANISM: Artificial sequence
<220> FEATURE:
<223> OTHER INFORMATION: Synthetic peptide of Formula (I). Sequence is
      linked to Y1 at the N-terminus and to Y2 at the C-terminus. Y1 and
      Y2 are each either absent or a peptide comprising a cationic
      polymer of basic amino acids, provided that at least one of Y1 and
      Y2 is present.

<400> SEQUENCE: 3

Trp Tyr Lys Trp Met Lys Lys His His
1               5

<210> SEQ ID NO 4
<211> LENGTH: 9
<212> TYPE: PRT
<213> ORGANISM: Artificial sequence
<220> FEATURE:
<223> OTHER INFORMATION: Synthetic peptide of Formula (I). Sequence is
      linked to Y1 at the N-terminus and to Y2 at the C-terminus. Y1 and
      Y2 are each either absent or a peptide comprising a cationic
      polymer of basic amino acids, provided that at least one of Y1 and
      Y2 is present.

<400> SEQUENCE: 4

Trp Tyr Lys Trp Met Lys Lys Ala Ala
1               5

<210> SEQ ID NO 5
<211> LENGTH: 7
<212> TYPE: PRT
<213> ORGANISM: Artificial sequence
<220> FEATURE:
<223> OTHER INFORMATION: Synthetic peptide of Formula (I). Sequence is
      linked to Y1 at the N-terminus and to Y2 at the C-terminus. Y1 and
      Y2 are each either absent or a peptide comprising a cationic
      polymer of basic amino acids, provided that at least one of Y1 and
      Y2 is present.

<400> SEQUENCE: 5

Trp Tyr Lys Trp Met Lys Lys
1               5

<210> SEQ ID NO 6
<211> LENGTH: 18
<212> TYPE: PRT
```

```
<213> ORGANISM: Artificial sequence
<220> FEATURE:
<223> OTHER INFORMATION: Synthetic peptide

<400> SEQUENCE: 6

Trp Tyr Lys Trp Met Lys Lys His His Arg Arg Arg Arg Arg Arg
1               5                   10                  15

Arg Arg

<210> SEQ ID NO 7
<211> LENGTH: 18
<212> TYPE: PRT
<213> ORGANISM: Artificial sequence
<220> FEATURE:
<223> OTHER INFORMATION: Synthetic peptide

<400> SEQUENCE: 7

Trp Tyr Lys Trp Met Lys Lys Ala Ala Arg Arg Arg Arg Arg Arg
1               5                   10                  15

Arg Arg

<210> SEQ ID NO 8
<211> LENGTH: 16
<212> TYPE: PRT
<213> ORGANISM: Artificial sequence
<220> FEATURE:
<223> OTHER INFORMATION: Synthetic peptide

<400> SEQUENCE: 8

Trp Tyr Lys Trp Met Lys Lys Arg Arg Arg Arg Arg Arg Arg Arg
1               5                   10                  15

<210> SEQ ID NO 9
<211> LENGTH: 9
<212> TYPE: PRT
<213> ORGANISM: Artificial sequence
<220> FEATURE:
<223> OTHER INFORMATION: Synthetic peptide

<400> SEQUENCE: 9

Arg Arg Arg Arg Arg Arg Arg Arg Arg
1               5

<210> SEQ ID NO 10
<211> LENGTH: 9
<212> TYPE: PRT
<213> ORGANISM: Artificial sequence
<220> FEATURE:
<223> OTHER INFORMATION: Synthetic peptide

<400> SEQUENCE: 10

Trp Tyr Lys Trp Met Lys Lys His His
1               5

<210> SEQ ID NO 11
<211> LENGTH: 10
<212> TYPE: PRT
<213> ORGANISM: Artificial sequence
<220> FEATURE:
<223> OTHER INFORMATION: Synthetic peptide

<400> SEQUENCE: 11

Trp Tyr Lys Trp Met Lys Lys His His Arg
1               5                   10
```

```
<210> SEQ ID NO 12
<211> LENGTH: 9
<212> TYPE: PRT
<213> ORGANISM: Artificial sequence
<220> FEATURE:
<223> OTHER INFORMATION: Synthetic peptide

<400> SEQUENCE: 12

Trp Tyr Lys Trp Met Lys Lys Ala Ala
1               5

<210> SEQ ID NO 13
<211> LENGTH: 10
<212> TYPE: PRT
<213> ORGANISM: Artificial sequence
<220> FEATURE:
<223> OTHER INFORMATION: Synthetic peptide

<400> SEQUENCE: 13

Trp Tyr Lys Trp Met Lys Lys Ala Ala Arg
1               5                   10

<210> SEQ ID NO 14
<211> LENGTH: 7
<212> TYPE: PRT
<213> ORGANISM: Artificial sequence
<220> FEATURE:
<223> OTHER INFORMATION: Synthetic peptide

<400> SEQUENCE: 14

Trp Tyr Lys Trp Met Lys Lys
1               5

<210> SEQ ID NO 15
<211> LENGTH: 8
<212> TYPE: PRT
<213> ORGANISM: Artificial sequence
<220> FEATURE:
<223> OTHER INFORMATION: Synthetic peptide

<400> SEQUENCE: 15

Trp Tyr Lys Trp Met Lys Lys Arg
1               5

<210> SEQ ID NO 16
<211> LENGTH: 9
<212> TYPE: PRT
<213> ORGANISM: Artificial sequence
<220> FEATURE:
<223> OTHER INFORMATION: Synthetic peptide of Formula (II). Sequence is
      linked to Y3 at the N-terminus and to Y4 at the C-terminus. Y3 &
      Y4 are each either absent or a peptide comprising a cell
      penetrating moiety, provided that at least one of Y3 and Y4 is
      present.
<220> FEATURE:
<221> NAME/KEY: VARIANT
<222> LOCATION: (1)..(9)
<223> OTHER INFORMATION: At least the N-terminal and C-terminal amino
      acids of the synthetic peptide of Formula (II), that is SEQ ID NO:
      16 with at least one of Y3 and Y4 present, are in the
      D-conformation.

<400> SEQUENCE: 16

Trp Tyr Lys Trp Met Lys Lys His His
1               5

<210> SEQ ID NO 17
<211> LENGTH: 9
<212> TYPE: PRT
```

```
<213> ORGANISM: Artificial sequence
<220> FEATURE:
<223> OTHER INFORMATION: Synthetic peptide of Formula (II). Sequence is
      linked to Y3 at the N-terminus and to Y4 at the C-terminus. Y3 &
      Y4 are each either absent or a peptide comprising a cell
      penetrating moiety, provided that at least one of Y3 and Y4 is
      present.
<220> FEATURE:
<221> NAME/KEY: VARIANT
<222> LOCATION: (1)..(9)
<223> OTHER INFORMATION: At least the N-terminal and C-terminal amino
      acids of the synthetic peptide of Formula (II), that is SEQ ID NO:
      17 with at least one of Y3 and Y4 present, are in the
      D-conformation.

<400> SEQUENCE: 17

Trp Tyr Lys Trp Met Lys Lys Ala Ala
1               5

<210> SEQ ID NO 18
<211> LENGTH: 7
<212> TYPE: PRT
<213> ORGANISM: Artificial sequence
<220> FEATURE:
<223> OTHER INFORMATION: Synthetic peptide of Formula (II). Sequence is
      linked to Y3 at the N-terminus and to Y4 at the C-terminus. Y3 &
      Y4 are each either absent or a peptide comprising a cell
      penetrating moiety, provided that at least one of Y3 and Y4 is
      present.
<220> FEATURE:
<221> NAME/KEY: VARIANT
<222> LOCATION: (1)..(7)
<223> OTHER INFORMATION: At least the N-terminal and C-terminal amino
      acids of the synthetic peptide of Formula (II), that is SEQ ID NO:
      18 with at least one of Y3 and Y4 present, are in the
      D-conformation.

<400> SEQUENCE: 18

Trp Tyr Lys Trp Met Lys Lys
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic peptide

<400> SEQUENCE: 19

Trp Cys Lys Trp Leu Asp Arg His Gly
1               5

<210> SEQ ID NO 20
<211> LENGTH: 9
<212> TYPE: PRT
<213> ORGANISM: Artificial sequence
<220> FEATURE:
<223> OTHER INFORMATION: Synthetic peptide

<400> SEQUENCE: 20

Trp Tyr Lys Trp Val Lys Lys His His
1               5

<210> SEQ ID NO 21
<211> LENGTH: 9
<212> TYPE: PRT
<213> ORGANISM: Artificial sequence
<220> FEATURE:
<223> OTHER INFORMATION: Synthetic peptide

<400> SEQUENCE: 21
```

Trp Tyr Lys Trp Ile Lys Lys His His
1               5

<210> SEQ ID NO 22
<211> LENGTH: 9
<212> TYPE: PRT
<213> ORGANISM: Artificial sequence
<220> FEATURE:
<223> OTHER INFORMATION: Synthetic peptide

<400> SEQUENCE: 22

Trp Tyr Lys Trp Met Arg Lys His His
1               5

<210> SEQ ID NO 23
<211> LENGTH: 9
<212> TYPE: PRT
<213> ORGANISM: Artificial sequence
<220> FEATURE:
<223> OTHER INFORMATION: Synthetic peptide

<400> SEQUENCE: 23

Trp Tyr Lys Trp Met Lys Arg His His
1               5

<210> SEQ ID NO 24
<211> LENGTH: 9
<212> TYPE: PRT
<213> ORGANISM: Artificial sequence
<220> FEATURE:
<223> OTHER INFORMATION: Synthetic peptide

<400> SEQUENCE: 24

Trp Tyr Lys Trp Met Arg Arg His His
1               5

<210> SEQ ID NO 25
<211> LENGTH: 9
<212> TYPE: PRT
<213> ORGANISM: Artificial sequence
<220> FEATURE:
<223> OTHER INFORMATION: Synthetic peptide

<400> SEQUENCE: 25

Trp Tyr Lys Trp Met Lys Lys Thr His
1               5

<210> SEQ ID NO 26
<211> LENGTH: 9
<212> TYPE: PRT
<213> ORGANISM: Artificial sequence
<220> FEATURE:
<223> OTHER INFORMATION: Synthetic peptide

<400> SEQUENCE: 26

Trp Tyr Lys Trp Met Lys Lys His Thr
1               5

<210> SEQ ID NO 27
<211> LENGTH: 9
<212> TYPE: PRT
<213> ORGANISM: Artificial sequence
<220> FEATURE:
<223> OTHER INFORMATION: Synthetic peptide

<400> SEQUENCE: 27

Trp Tyr Lys Trp Met Lys Lys Thr Thr
1               5

<210> SEQ ID NO 28
<211> LENGTH: 9
<212> TYPE: PRT
<213> ORGANISM: Artificial sequence
<220> FEATURE:
<223> OTHER INFORMATION: Synthetic peptide

<400> SEQUENCE: 28

Trp Cys Lys Trp Met Lys Lys His His
1               5

<210> SEQ ID NO 29
<211> LENGTH: 9
<212> TYPE: PRT
<213> ORGANISM: Artificial sequence
<220> FEATURE:
<223> OTHER INFORMATION: Synthetic peptide

<400> SEQUENCE: 29

Trp Cys Lys Trp Met Arg Lys His His
1               5

<210> SEQ ID NO 30
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa may be present or absent. If present, Xaa
      is Arg or Gln
<220> FEATURE:
<221> NAME/KEY: VARIANT
<222> LOCATION: (3)..(3)
<223> OTHER INFORMATION: Xaa is Ile or Leu
<220> FEATURE:
<221> NAME/KEY: VARIANT
<222> LOCATION: (4)..(4)
<223> OTHER INFORMATION: Xaa is Lys or Arg
<220> FEATURE:
<221> NAME/KEY: VARIANT
<222> LOCATION: (5)..(5)
<223> OTHER INFORMATION: Xaa is Ile or Leu
<220> FEATURE:
<221> NAME/KEY: VARIANT
<222> LOCATION: (10)..(10)
<223> OTHER INFORMATION: Xaa is Lys or Arg
<220> FEATURE:
<221> NAME/KEY: VARIANT
<222> LOCATION: (11)..(11)
<223> OTHER INFORMATION: Xaa is Lys or Arg
<220> FEATURE:
<221> NAME/KEY: VARIANT
<222> LOCATION: (13)..(13)
<223> OTHER INFORMATION: Xaa is Lys or Arg
<220> FEATURE:
<221> NAME/KEY: VARIANT
<222> LOCATION: (15)..(16)
<223> OTHER INFORMATION: Xaa is Lys or Arg

<400> SEQUENCE: 30

Xaa Gln Xaa Xaa Xaa Trp Phe Gln Asn Xaa Xaa Met Xaa Trp Xaa Xaa
1               5                   10                  15

<210> SEQ ID NO 31
<211> LENGTH: 25
<212> TYPE: PRT

<213> ORGANISM: Artificial sequence
<220> FEATURE:
<223> OTHER INFORMATION: Synthetic peptide

<400> SEQUENCE: 31

Trp Tyr Lys Trp Met Lys Lys His His Arg Gln Ile Lys Ile Trp Phe
1               5                   10                  15

Gln Asn Arg Arg Met Lys Trp Lys Lys
            20                  25

<210> SEQ ID NO 32
<211> LENGTH: 25
<212> TYPE: PRT
<213> ORGANISM: Artificial sequence
<220> FEATURE:
<223> OTHER INFORMATION: Synthetic peptide

<400> SEQUENCE: 32

Trp Tyr Lys Trp Met Lys Lys Ala Ala Arg Gln Ile Lys Ile Trp Phe
1               5                   10                  15

Gln Asn Arg Arg Met Lys Trp Lys Lys
            20                  25

<210> SEQ ID NO 33
<211> LENGTH: 23
<212> TYPE: PRT
<213> ORGANISM: Artificial sequence
<220> FEATURE:
<223> OTHER INFORMATION: Synthetic peptide

<400> SEQUENCE: 33

Trp Tyr Lys Trp Met Lys Lys Arg Gln Ile Lys Ile Trp Phe Gln Asn
1               5                   10                  15

Arg Arg Met Lys Trp Lys Lys
            20

<210> SEQ ID NO 34
<211> LENGTH: 24
<212> TYPE: PRT
<213> ORGANISM: Artificial sequence
<220> FEATURE:
<223> OTHER INFORMATION: Synthetic peptide

<400> SEQUENCE: 34

Trp Tyr Lys Trp Met Lys Lys His His Arg Gln Ile Lys Ile Trp Phe
1               5                   10                  15

Gln Asn Arg Arg Met Lys Trp Lys
            20

<210> SEQ ID NO 35
<211> LENGTH: 24
<212> TYPE: PRT
<213> ORGANISM: Artificial sequence
<220> FEATURE:
<223> OTHER INFORMATION: Synthetic peptide

<400> SEQUENCE: 35

Trp Tyr Lys Trp Met Lys Lys Ala Ala Arg Gln Ile Lys Ile Trp Phe
1               5                   10                  15

Gln Asn Arg Arg Met Lys Trp Lys
            20

<210> SEQ ID NO 36
<211> LENGTH: 22

```
<212> TYPE: PRT
<213> ORGANISM: Artificial sequence
<220> FEATURE:
<223> OTHER INFORMATION: Synthetic peptide

<400> SEQUENCE: 36

Trp Tyr Lys Trp Met Lys Lys Arg Gln Ile Lys Ile Trp Phe Gln Asn
1               5                   10                  15

Arg Arg Met Lys Trp Lys
            20

<210> SEQ ID NO 37
<211> LENGTH: 9
<212> TYPE: PRT
<213> ORGANISM: Artificial sequence
<220> FEATURE:
<223> OTHER INFORMATION: Synthetic peptide

<400> SEQUENCE: 37

Trp Cys Lys Trp Met Lys Arg His His
1               5

<210> SEQ ID NO 38
<211> LENGTH: 9
<212> TYPE: PRT
<213> ORGANISM: Artificial sequence
<220> FEATURE:
<223> OTHER INFORMATION: Synthetic peptide

<400> SEQUENCE: 38

Trp Cys Lys Trp Met Arg Arg His His
1               5

<210> SEQ ID NO 39
<211> LENGTH: 9
<212> TYPE: PRT
<213> ORGANISM: Artificial sequence
<220> FEATURE:
<223> OTHER INFORMATION: Synthetic peptide

<400> SEQUENCE: 39

Trp Tyr Lys Trp Met Lys Arg Thr His
1               5

<210> SEQ ID NO 40
<211> LENGTH: 9
<212> TYPE: PRT
<213> ORGANISM: Artificial sequence
<220> FEATURE:
<223> OTHER INFORMATION: Synthetic peptide

<400> SEQUENCE: 40

Trp Tyr Lys Trp Met Arg Lys Thr His
1               5

<210> SEQ ID NO 41
<211> LENGTH: 9
<212> TYPE: PRT
<213> ORGANISM: Artificial sequence
<220> FEATURE:
<223> OTHER INFORMATION: Synthetic peptide

<400> SEQUENCE: 41

Trp Tyr Lys Trp Met Arg Arg Thr His
1               5
```

```
<210> SEQ ID NO 42
<211> LENGTH: 9
<212> TYPE: PRT
<213> ORGANISM: Artificial sequence
<220> FEATURE:
<223> OTHER INFORMATION: Synthetic peptide

<400> SEQUENCE: 42

Trp Tyr Lys Trp Met Arg Lys His Thr
1               5

<210> SEQ ID NO 43
<211> LENGTH: 9
<212> TYPE: PRT
<213> ORGANISM: Artificial sequence
<220> FEATURE:
<223> OTHER INFORMATION: Synthetic peptide

<400> SEQUENCE: 43

Trp Tyr Lys Trp Met Lys Arg His Thr
1               5

<210> SEQ ID NO 44
<211> LENGTH: 9
<212> TYPE: PRT
<213> ORGANISM: Artificial sequence
<220> FEATURE:
<223> OTHER INFORMATION: Synthetic peptide

<400> SEQUENCE: 44

Trp Tyr Lys Trp Met Arg Arg His Thr
1               5

<210> SEQ ID NO 45
<211> LENGTH: 9
<212> TYPE: PRT
<213> ORGANISM: Artificial sequence
<220> FEATURE:
<223> OTHER INFORMATION: Synthetic peptide

<400> SEQUENCE: 45

Trp Tyr Lys Trp Met Arg Arg Thr Thr
1               5

<210> SEQ ID NO 46
<211> LENGTH: 9
<212> TYPE: PRT
<213> ORGANISM: Artificial sequence
<220> FEATURE:
<223> OTHER INFORMATION: Synthetic peptide

<400> SEQUENCE: 46

Trp Tyr Lys Trp Leu Arg Lys His His
1               5

<210> SEQ ID NO 47
<211> LENGTH: 9
<212> TYPE: PRT
<213> ORGANISM: Artificial sequence
<220> FEATURE:
<223> OTHER INFORMATION: Synthetic peptide

<400> SEQUENCE: 47

Trp Tyr Lys Trp Leu Lys Arg His His
1               5

<210> SEQ ID NO 48
```

```
<211> LENGTH: 8
<212> TYPE: PRT
<213> ORGANISM: Artificial sequence
<220> FEATURE:
<223> OTHER INFORMATION: Synthetic peptide

<400> SEQUENCE: 48

Trp Tyr Lys Trp Met Lys Lys His
1               5

<210> SEQ ID NO 49
<211> LENGTH: 9
<212> TYPE: PRT
<213> ORGANISM: Artificial sequence
<220> FEATURE:
<223> OTHER INFORMATION: Synthetic peptide

<400> SEQUENCE: 49

Trp Cys Lys Trp Leu Asp Arg Ala Gly
1               5

<210> SEQ ID NO 50
<211> LENGTH: 9
<212> TYPE: PRT
<213> ORGANISM: Artificial sequence
<220> FEATURE:
<223> OTHER INFORMATION: Synthetic peptide

<400> SEQUENCE: 50

Trp Tyr Lys Trp Val Lys Lys Ala Ala
1               5

<210> SEQ ID NO 51
<211> LENGTH: 9
<212> TYPE: PRT
<213> ORGANISM: Artificial sequence
<220> FEATURE:
<223> OTHER INFORMATION: Synthetic peptide

<400> SEQUENCE: 51

Trp Tyr Lys Trp Ile Lys Lys Ala Ala
1               5

<210> SEQ ID NO 52
<211> LENGTH: 9
<212> TYPE: PRT
<213> ORGANISM: Artificial sequence
<220> FEATURE:
<223> OTHER INFORMATION: Synthetic peptide

<400> SEQUENCE: 52

Trp Tyr Lys Trp Met Arg Lys Ala Ala
1               5

<210> SEQ ID NO 53
<211> LENGTH: 9
<212> TYPE: PRT
<213> ORGANISM: Artificial sequence
<220> FEATURE:
<223> OTHER INFORMATION: Synthetic peptide

<400> SEQUENCE: 53

Trp Tyr Lys Trp Met Lys Arg Ala Ala
1               5

<210> SEQ ID NO 54
<211> LENGTH: 9
```

```
<212> TYPE: PRT
<213> ORGANISM: Artificial sequence
<220> FEATURE:
<223> OTHER INFORMATION: Synthetic peptide

<400> SEQUENCE: 54

Trp Tyr Lys Trp Met Arg Arg Ala Ala
1               5

<210> SEQ ID NO 55
<211> LENGTH: 9
<212> TYPE: PRT
<213> ORGANISM: Artificial sequence
<220> FEATURE:
<223> OTHER INFORMATION: Synthetic peptide

<400> SEQUENCE: 55

Trp Tyr Lys Trp Met Lys Lys Thr Ala
1               5

<210> SEQ ID NO 56
<211> LENGTH: 9
<212> TYPE: PRT
<213> ORGANISM: Artificial sequence
<220> FEATURE:
<223> OTHER INFORMATION: Synthetic peptide

<400> SEQUENCE: 56

Trp Tyr Lys Trp Met Lys Lys Ala Thr
1               5

<210> SEQ ID NO 57
<211> LENGTH: 9
<212> TYPE: PRT
<213> ORGANISM: Artificial sequence
<220> FEATURE:
<223> OTHER INFORMATION: Synthetic peptide

<400> SEQUENCE: 57

Trp Cys Lys Trp Met Lys Lys Ala Ala
1               5

<210> SEQ ID NO 58
<211> LENGTH: 9
<212> TYPE: PRT
<213> ORGANISM: Artificial sequence
<220> FEATURE:
<223> OTHER INFORMATION: Synthetic peptide

<400> SEQUENCE: 58

Trp Cys Lys Trp Met Arg Lys Ala Ala
1               5

<210> SEQ ID NO 59
<211> LENGTH: 9
<212> TYPE: PRT
<213> ORGANISM: Artificial sequence
<220> FEATURE:
<223> OTHER INFORMATION: Synthetic peptide

<400> SEQUENCE: 59

Trp Cys Lys Trp Met Lys Arg Ala Ala
1               5

<210> SEQ ID NO 60
<211> LENGTH: 9
<212> TYPE: PRT
```

```
<213> ORGANISM: Artificial sequence
<220> FEATURE:
<223> OTHER INFORMATION: Synthetic peptide

<400> SEQUENCE: 60

Trp Cys Lys Trp Met Arg Arg Ala Ala
1               5

<210> SEQ ID NO 61
<211> LENGTH: 9
<212> TYPE: PRT
<213> ORGANISM: Artificial sequence
<220> FEATURE:
<223> OTHER INFORMATION: Synthetic peptide

<400> SEQUENCE: 61

Trp Tyr Lys Trp Met Lys Arg Thr Ala
1               5

<210> SEQ ID NO 62
<211> LENGTH: 9
<212> TYPE: PRT
<213> ORGANISM: Artificial sequence
<220> FEATURE:
<223> OTHER INFORMATION: Synthetic peptide

<400> SEQUENCE: 62

Trp Tyr Lys Trp Met Arg Lys Thr Ala
1               5

<210> SEQ ID NO 63
<211> LENGTH: 9
<212> TYPE: PRT
<213> ORGANISM: Artificial sequence
<220> FEATURE:
<223> OTHER INFORMATION: Synthetic peptide

<400> SEQUENCE: 63

Trp Tyr Lys Trp Met Arg Arg Thr Ala
1               5

<210> SEQ ID NO 64
<211> LENGTH: 9
<212> TYPE: PRT
<213> ORGANISM: Artificial sequence
<220> FEATURE:
<223> OTHER INFORMATION: Synthetic peptide

<400> SEQUENCE: 64

Trp Tyr Lys Trp Met Arg Lys Ala Thr
1               5

<210> SEQ ID NO 65
<211> LENGTH: 9
<212> TYPE: PRT
<213> ORGANISM: Artificial sequence
<220> FEATURE:
<223> OTHER INFORMATION: Synthetic peptide

<400> SEQUENCE: 65

Trp Tyr Lys Trp Met Lys Arg Ala Thr
1               5

<210> SEQ ID NO 66
<211> LENGTH: 9
<212> TYPE: PRT
<213> ORGANISM: Artificial sequence
```

```
<220> FEATURE:
<223> OTHER INFORMATION: Synthetic peptide

<400> SEQUENCE: 66

Trp Tyr Lys Trp Met Arg Arg Ala Thr
1               5

<210> SEQ ID NO 67
<211> LENGTH: 9
<212> TYPE: PRT
<213> ORGANISM: Artificial sequence
<220> FEATURE:
<223> OTHER INFORMATION: Synthetic peptide

<400> SEQUENCE: 67

Trp Tyr Lys Trp Leu Arg Lys Ala Ala
1               5

<210> SEQ ID NO 68
<211> LENGTH: 9
<212> TYPE: PRT
<213> ORGANISM: Artificial sequence
<220> FEATURE:
<223> OTHER INFORMATION: Synthetic peptide

<400> SEQUENCE: 68

Trp Tyr Lys Trp Leu Lys Arg Ala Ala
1               5

<210> SEQ ID NO 69
<211> LENGTH: 8
<212> TYPE: PRT
<213> ORGANISM: Artificial sequence
<220> FEATURE:
<223> OTHER INFORMATION: Synthetic peptide

<400> SEQUENCE: 69

Trp Tyr Lys Trp Met Lys Lys Ala
1               5

<210> SEQ ID NO 70
<211> LENGTH: 15
<212> TYPE: PRT
<213> ORGANISM: Artificial sequence
<220> FEATURE:
<223> OTHER INFORMATION: Synthetic peptide

<400> SEQUENCE: 70

Gln Ile Lys Ile Trp Phe Gln Asn Arg Arg Met Lys Trp Lys Lys
1               5                   10                  15

<210> SEQ ID NO 71
<211> LENGTH: 15
<212> TYPE: PRT
<213> ORGANISM: Artificial sequence
<220> FEATURE:
<223> OTHER INFORMATION: Synthetic peptide

<400> SEQUENCE: 71

Gln Ile Arg Ile Trp Phe Gln Asn Arg Arg Met Lys Trp Lys Lys
1               5                   10                  15

<210> SEQ ID NO 72
<211> LENGTH: 15
<212> TYPE: PRT
<213> ORGANISM: Artificial sequence
<220> FEATURE:
```

<223> OTHER INFORMATION: Synthetic peptide

<400> SEQUENCE: 72

Gln Ile Lys Ile Trp Phe Gln Asn Lys Arg Met Lys Trp Lys Lys
1               5                   10                  15

<210> SEQ ID NO 73
<211> LENGTH: 15
<212> TYPE: PRT
<213> ORGANISM: Artificial sequence
<220> FEATURE:
<223> OTHER INFORMATION: Synthetic peptide

<400> SEQUENCE: 73

Gln Ile Lys Ile Trp Phe Gln Asn Lys Lys Met Lys Trp Lys Lys
1               5                   10                  15

<210> SEQ ID NO 74
<211> LENGTH: 15
<212> TYPE: PRT
<213> ORGANISM: Artificial sequence
<220> FEATURE:
<223> OTHER INFORMATION: Synthetic peptide

<400> SEQUENCE: 74

Gln Ile Arg Ile Trp Phe Gln Asn Arg Lys Met Lys Trp Lys Lys
1               5                   10                  15

<210> SEQ ID NO 75
<211> LENGTH: 15
<212> TYPE: PRT
<213> ORGANISM: Artificial sequence
<220> FEATURE:
<223> OTHER INFORMATION: Synthetic peptide

<400> SEQUENCE: 75

Gln Ile Arg Ile Trp Phe Gln Asn Arg Arg Met Arg Trp Lys Lys
1               5                   10                  15

<210> SEQ ID NO 76
<211> LENGTH: 15
<212> TYPE: PRT
<213> ORGANISM: Artificial sequence
<220> FEATURE:
<223> OTHER INFORMATION: Synthetic peptide

<400> SEQUENCE: 76

Gln Ile Arg Ile Trp Phe Gln Asn Arg Arg Met Lys Trp Arg Lys
1               5                   10                  15

<210> SEQ ID NO 77
<211> LENGTH: 15
<212> TYPE: PRT
<213> ORGANISM: Artificial sequence
<220> FEATURE:
<223> OTHER INFORMATION: Synthetic peptide

<400> SEQUENCE: 77

Gln Ile Arg Ile Trp Phe Gln Asn Arg Arg Met Lys Trp Lys Arg
1               5                   10                  15

<210> SEQ ID NO 78
<211> LENGTH: 15
<212> TYPE: PRT
<213> ORGANISM: Artificial sequence
<220> FEATURE:
<223> OTHER INFORMATION: Synthetic peptide

<400> SEQUENCE: 78

Gln Ile Arg Ile Trp Phe Gln Asn Arg Arg Met Lys Trp Arg Arg
1               5                   10                  15

<210> SEQ ID NO 79
<211> LENGTH: 15
<212> TYPE: PRT
<213> ORGANISM: Artificial sequence
<220> FEATURE:
<223> OTHER INFORMATION: Synthetic peptide

<400> SEQUENCE: 79

Gln Ile Arg Ile Trp Phe Gln Asn Arg Arg Met Lys Trp Lys Lys
1               5                   10                  15

<210> SEQ ID NO 80
<211> LENGTH: 15
<212> TYPE: PRT
<213> ORGANISM: Artificial sequence
<220> FEATURE:
<223> OTHER INFORMATION: Synthetic peptide

<400> SEQUENCE: 80

Gln Ile Lys Ile Trp Phe Gln Asn Arg Arg Met Lys Trp Arg Lys
1               5                   10                  15

<210> SEQ ID NO 81
<211> LENGTH: 15
<212> TYPE: PRT
<213> ORGANISM: Artificial sequence
<220> FEATURE:
<223> OTHER INFORMATION: Synthetic peptide

<400> SEQUENCE: 81

Gln Ile Arg Ile Trp Phe Gln Asn Lys Arg Met Lys Trp Arg Lys
1               5                   10                  15

<210> SEQ ID NO 82
<211> LENGTH: 15
<212> TYPE: PRT
<213> ORGANISM: Artificial sequence
<220> FEATURE:
<223> OTHER INFORMATION: Synthetic peptide

<400> SEQUENCE: 82

Gln Ile Lys Leu Trp Phe Gln Asn Arg Arg Met Lys Trp Lys Lys
1               5                   10                  15

<210> SEQ ID NO 83
<211> LENGTH: 15
<212> TYPE: PRT
<213> ORGANISM: Artificial sequence
<220> FEATURE:
<223> OTHER INFORMATION: Synthetic peptide

<400> SEQUENCE: 83

Gln Leu Lys Leu Trp Phe Gln Asn Arg Arg Met Lys Trp Lys Lys
1               5                   10                  15

<210> SEQ ID NO 84
<211> LENGTH: 15
<212> TYPE: PRT
<213> ORGANISM: Artificial sequence
<220> FEATURE:
<223> OTHER INFORMATION: Synthetic peptide

```
<400> SEQUENCE: 84

Gln Leu Arg Ile Trp Phe Gln Asn Arg Arg Met Lys Trp Lys Lys
1               5                   10                  15

<210> SEQ ID NO 85
<211> LENGTH: 7
<212> TYPE: PRT
<213> ORGANISM: Artificial sequence
<220> FEATURE:
<223> OTHER INFORMATION: Synthetic peptide (HOX hexapeptide sequence)

<400> SEQUENCE: 85

Trp Tyr Pro Trp Met Lys Lys
1               5

<210> SEQ ID NO 86
<211> LENGTH: 18
<212> TYPE: PRT
<213> ORGANISM: Artificial sequence
<220> FEATURE:
<223> OTHER INFORMATION: Control synthetic peptide HXR9

<400> SEQUENCE: 86

Trp Tyr Pro Trp Met Lys Lys His His Arg Arg Arg Arg Arg Arg
1               5                   10                  15

Arg Arg

<210> SEQ ID NO 87
<211> LENGTH: 18
<212> TYPE: PRT
<213> ORGANISM: Artificial sequence
<220> FEATURE:
<223> OTHER INFORMATION: Control synthetic peptide CXR9

<400> SEQUENCE: 87

Trp Tyr Pro Ala Met Lys Lys His His Arg Arg Arg Arg Arg Arg
1               5                   10                  15

Arg Arg

<210> SEQ ID NO 88
<211> LENGTH: 18
<212> TYPE: PRT
<213> ORGANISM: Artificial sequence
<220> FEATURE:
<223> OTHER INFORMATION: Control synthetic peptide HXR9AS7

<400> SEQUENCE: 88

Trp Tyr Pro Trp Met Lys Lys Ala Ala Arg Arg Arg Arg Arg Arg
1               5                   10                  15

Arg Arg

<210> SEQ ID NO 89
<211> LENGTH: 16
<212> TYPE: PRT
<213> ORGANISM: Artificial sequence
<220> FEATURE:
<223> OTHER INFORMATION: Control synthetic peptide HXR9noH

<400> SEQUENCE: 89

Trp Tyr Pro Trp Met Lys Lys Arg Arg Arg Arg Arg Arg Arg Arg
1               5                   10                  15

<210> SEQ ID NO 90
<211> LENGTH: 6
```

```
<212> TYPE: PRT
<213> ORGANISM: Artificial sequence
<220> FEATURE:
<223> OTHER INFORMATION: Synthetic peptide

<400> SEQUENCE: 90

Arg Arg Arg Arg Arg Arg
1               5

<210> SEQ ID NO 91
<211> LENGTH: 7
<212> TYPE: PRT
<213> ORGANISM: Artificial sequence
<220> FEATURE:
<223> OTHER INFORMATION: Synthetic peptide

<400> SEQUENCE: 91

Arg Arg Arg Arg Arg Arg Arg
1               5

<210> SEQ ID NO 92
<211> LENGTH: 8
<212> TYPE: PRT
<213> ORGANISM: Artificial sequence
<220> FEATURE:
<223> OTHER INFORMATION: Synthetic peptide

<400> SEQUENCE: 92

Arg Arg Arg Arg Arg Arg Arg Arg
1               5

<210> SEQ ID NO 93
<211> LENGTH: 10
<212> TYPE: PRT
<213> ORGANISM: Artificial sequence
<220> FEATURE:
<223> OTHER INFORMATION: Synthetic peptide

<400> SEQUENCE: 93

Arg Arg Arg Arg Arg Arg Arg Arg Arg Arg
1               5                   10
```

The invention claimed is:

1. A peptide comprising formula (I):

$$Y^1X^1X^2KWX^3X^4X^5X^6X^7Y^2 \quad (I)$$

wherein the sequence $X^1$ to $X^7$ is selected from WYKWMKKHH (SEQ ID NO: 10), WYKWMKKAA (SEQ ID NO: 12), and WYKWMKK (SEQ ID NO: 14); and $Y^1$ and $Y^2$ are each either absent or a peptide comprising a cationic polymer of basic amino acids, provided that at least one of $Y^1$ and $Y^2$ is present.

2. The peptide according to claim 1, wherein $Y^1$ and/or $Y^2$ is a cell penetration moiety.

3. The peptide according to claim 1, wherein $Y^1$ and/or $Y^2$ is a homopolymer of basic amino acids.

4. The peptide according to claim 1, wherein the basic amino acids of $Y^1$ and/or $Y^2$ are selected from arginine, lysine and histidine.

5. The peptide according to claim 1, wherein $Y^1$ and/or $Y^2$ is a polyarginine peptide.

6. The peptide according to claim 5, wherein $Y^1$ and/or $Y^2$ is $(Arg)_{6-12}$ (SEQ ID NO: 90, SEQ ID NO: 91, SEQ ID NO: 92, SEQ ID NO: 9, SEQ ID NO:93, SEQ ID NO: 1, or SEQ ID NO: 2 respectively).

7. The peptide according to claim 6, wherein $Y^1$ and/or $Y^2$ is $(Arg)_9$ (SEQ ID NO:9).

8. A peptide comprising formula (II):

$$Y^3X^1X^2KWX^3X^4X^5X^6X^7Y^4 \quad (II)$$

wherein the sequence $X^1$ to $X^7$ is selected from WYKWMKKHH (SEQ ID NO: 10), WYKWMKKAA (SEQ ID NO: 12), and WYKWMKK (SEQ ID NO: 14); and $Y^3$ and $Y^4$ are each either absent or a peptide comprising a sequence comprising a cell penetration moiety, provided that at least one of $Y^3$ and $Y^4$ is present;

wherein at least the N-terminal and C-terminal amino acids of said peptide are in the D-conformation.

9. The peptide according to claim 8, wherein $Y^3$ and/or $Y^4$ is a peptide comprising a cationic polymer of basic amino acids in relation to $Y^1$ and/or $Y^2$.

10. The peptide according to claim 1, wherein said peptide has the sequence selected from:

WYKWMKKHHRRRRRRRRR; (SEQ ID NO: 6)

WYKWMKKAARRRRRRRRR; (SEQ ID NO: 7)
and

WYKWMKKRRRRRRRRR. (SEQ ID NO: 8)

11. The peptide according to claim 8, wherein said cell penetration moiety comprises the amino acid sequence $$X^9QX^{10}X^{11}X^{12}WFQNX^{13}X^{14}MX^{15}WX^{16}X^{17}$$ (SEQ ID NO: 30)

wherein
$X^9$ is R or Q or absent;
$X^{10}$, $X^{12}$ are each independently I or L; and
$X^{11}$, $X^{13}$, $X^{14}$, $X^{15}$, $X^{16}$ and $X^{17}$ are each independently K or R.

12. The peptide according to claim 11, wherein said cell penetration moiety comprises the amino acid sequence:

QIKIWFQNRRMKWKK; (SEQ ID NO: 70)

QIRIWFQNRRMKWKK; (SEQ ID NO: 71)

QIKIWFQNKRMKWKK; (SEQ ID NO: 72)

QIKIWFQNKKMKWKK; (SEQ ID NO: 73)

QIRIWFQNRKMKWKK; (SEQ ID NO: 74)

QIRIWFQNRRMRWKK; (SEQ ID NO: 75)

QIRIWFQNRRMKWRK; (SEQ ID NO: 76)

QIRIWFQNRRMKWKR; (SEQ ID NO: 77)

QIRIWFQNRRMKWRR; (SEQ ID NO: 78)

QIRIWFQNRRMKWKK; (SEQ ID NO: 79)

QIKIWFQNRRMKWRK; (SEQ ID NO: 80)

QIRIWFQNKRMKWRK; (SEQ ID NO: 81)

QIKLWFQNRRMKWKK, (SEQ ID NO: 82)

QLKLWFQNRRMKWKK; (SEQ ID NO: 83)
or

QLRIWFQNRRMKWKK. (SEQ ID NO: 84)

13. The peptide according to claim 8, wherein said peptide has the sequence selected from:

WYKWMKKHHRQIKIWFQNRRMKWK; (SEQ ID NO: 31)

WYKWMKKHHRQIKIWFQNRRMKWKK; (SEQ ID NO: 34)

WYKWMKKHHRQIKIWFQNRRMKWK; (SEQ ID NO: 32)

WYKWMKKHHRQIKIWFQNRRMKWKK; (SEQ ID NO: 35)

WYKWMKKHHRQIKIWFQNRRMKWK; (SEQ ID NO: 33)
and

WYKWMKKHHRQIKIWFQNRRMKWKK. (SEQ ID NO: 36)

14. A pharmaceutical composition comprising a peptide according to claim 1, and one or more pharmaceutically acceptable excipients, diluents and/or carriers.

15. The pharmaceutical composition according to claim 14, further comprising one or more additional therapeutic agents.

16. The pharmaceutical composition according to claim 15, wherein the one or more additional therapeutic agents is selected from cytotoxic agents, and chemotherapeutic agents, and combinations thereof.

17. The peptide according to claim 1 for use as a pharmaceutical.

18. A method for reducing the side effects of a cytotoxic or chemotherapeutic agent, the method comprising administering to a subject in need thereof a therapeutically effective amount of the peptide of claim 1.

19. A method for maintaining or expanding a stem cell population in vivo, the method comprising administering to a subject in need thereof a therapeutically effective amount of the peptide of claim 1.

20. A medicament for treating or preventing a disorder in which aberrant cell division occurs via interaction of HOX and PBX, the medicament comprising the peptide of claim 1 and one or more pharmaceutically acceptable excipients, diluents and/or carriers.

21. A method for preventing or treating a condition or disorder in which aberrant cell division occurs via interaction of HOX and PBX, which method comprises administering to a subject in need thereof a therapeutically effective amount of the peptide as defined in claim 1.

22. The method according to claim 21, wherein said subject is also administered a cytotoxic or chemotherapeutic agent.

23. A method of maintaining or expanding stem cells ex vivo comprising contacting said stem cells with a peptide as defined in claim 1.

24. The method of claim 21, wherein the condition or disorder is a cancer which involves expression of HOX and PBX genes.

25. The method of claim 21, wherein said cells express one or more HOX genes.

26. The method of claim 21, wherein PBX does not act as an oncogene in said cells.

* * * * *